United States Patent
Zucherman et al.

(10) Patent No.: US 6,712,819 B2
(45) Date of Patent: *Mar. 30, 2004

(54) MATING INSERTION INSTRUMENTS FOR SPINAL IMPLANTS AND METHODS OF USE

(75) Inventors: James F. Zucherman, San Francisco, CA (US); Ken Y. Hsu, San Francisco, CA (US); Charles J. Winslow, Walnut Creek, CA (US); John Flynn, Concord, CA (US)

(73) Assignee: St. Francis Medical Technologies, Inc., Concord, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/981,859
(22) Filed: Oct. 18, 2001
(65) Prior Publication Data

US 2002/0099377 A1 Jul. 25, 2002

Related U.S. Application Data

(63) Continuation-in-part of application No. 09/799,470, filed on Mar. 5, 2001, which is a continuation-in-part of application No. 09/473,173, filed on Dec. 28, 1999, now Pat. No. 6,235,030, which is a continuation of application No. 09/179,570, filed on Oct. 27, 1998, now Pat. No. 6,048,342, which is a continuation-in-part of application No. 09/175,645, filed on Oct. 20, 1998, now Pat. No. 6,068,630.
(60) Provisional application No. 60/306,101, filed on Jul. 17, 2001.

(51) Int. Cl.$^7$ ............................................. A61B 17/70
(52) U.S. Cl. ....................................................... 606/61
(58) Field of Search ........................... 606/61, 99, 104; 623/17.11–17.16

(56) References Cited

U.S. PATENT DOCUMENTS

| 2,456,806 A | 12/1948 | Wolffe |
| 2,677,369 A | 5/1954 | Knowles |
| 3,426,364 A | 2/1969 | Lumb |
| 3,648,691 A | 3/1972 | Lumb et al. |
| 3,867,728 A | 2/1975 | Stubstad et al. |
| 3,875,595 A | 4/1975 | Froning |
| 4,309,777 A | 1/1982 | Patil |
| 4,347,845 A | * 9/1982 | Mayfield |

(List continued on next page.)

FOREIGN PATENT DOCUMENTS

| CA | 2015507 | 1/1991 |
| DE | 2821678 A1 | 4/1980 |
| DE | 3113142 A1 | 1/1982 |
| EP | 140790 A2 | 10/1984 |
| EP | 146347 A1 | 12/1984 |

(List continued on next page.)

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819–1825, © 1997, Lippincott–Raven Publishers.

(List continued on next page.)

*Primary Examiner*—David O. Reip
(74) *Attorney, Agent, or Firm*—Fliesler Dubb Meyer and Lovejoy LLP

(57) ABSTRACT

Insertion instruments and a main body assembly and a universal wing to be inserted are provided, along with methods of using these instruments for the insertion of the spinal implants in patients to relieve the symptoms of, for example, spinal stenosis, injuries, and degenerative diseases of the spine. The instruments are simply designed and can be disassembled, making cleaning and sterilization easy and convenient. The instruments are designed to engage with and disengage from spinal implants easily, and use of the instrument in spinal implant surgery can be carried out with minimal surgical intervention and does not require general anesthesia. The main body assembly and the universal wing are designed to conveniently be secured to the insertion instruments. In an alternative embodiment the instrument can be nested and at least one instrument can include a handle provided at an angle.

62 Claims, 16 Drawing Sheets

U.S. PATENT DOCUMENTS

| | | |
|---|---|---|
| 4,349,921 A | 9/1982 | Kuntz |
| 4,369,769 A | 1/1983 | Edwards |
| 4,401,112 A | 8/1983 | Rezaian |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,604,995 A | 8/1986 | Stephens et al. |
| 4,611,582 A | 9/1986 | Duff |
| 4,636,217 A | 1/1987 | Ogilvie et al. |
| 4,643,178 A | 2/1987 | Nastari et al. |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,772,287 A | 9/1988 | Ray et al. |
| 4,790,303 A | 12/1988 | Steffee |
| 4,834,757 A | 5/1989 | Brantigan |
| 4,878,915 A | 11/1989 | Brantigan |
| 4,904,260 A | 2/1990 | Ray et al. |
| 4,904,261 A | 2/1990 | Dove et al. |
| 4,913,134 A | 4/1990 | Luque |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 5,011,484 A | 4/1991 | Breard |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,084,049 A | 1/1992 | Asher et al. |
| 5,092,866 A | 3/1992 | Breard et al. |
| 5,122,130 A | 6/1992 | Keller |
| 5,123,926 A | 6/1992 | Pisharodi |
| 5,167,662 A | 12/1992 | Hayes et al. |
| 5,180,381 A | 1/1993 | Aust et al. |
| 5,192,327 A | 3/1993 | Brantigan |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,352,225 A | 10/1994 | Yuan et al. |
| 5,387,213 A | 2/1995 | Breard et al. |
| 5,390,683 A | 2/1995 | Pisharodi |
| 5,395,372 A | 3/1995 | Holt et al. |
| 5,415,661 A | 5/1995 | Holmes |
| 5,443,514 A | 8/1995 | Steffee |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,514,180 A | 5/1996 | Heggeness et al. |
| 5,522,899 A | 6/1996 | Michelson |
| 5,534,028 A | 7/1996 | Bao et al. |
| 5,534,029 A | 7/1996 | Shima |
| 5,540,689 A | 7/1996 | Sanders et al. |
| 5,549,679 A | 8/1996 | Kuslich |
| 5,562,736 A | 10/1996 | Ray et al. |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,766,252 A | 6/1998 | Henry et al. |
| 5,800,438 A | 9/1998 | Tuke et al. |
| 5,824,098 A | 10/1998 | Stein |
| 5,865,846 A | 2/1999 | Bryan et al. |
| 5,885,299 A | 3/1999 | Winslow et al. |
| 5,888,224 A | 3/1999 | Beckers et al. |
| 5,888,226 A | 3/1999 | Rogozinski |
| 5,976,186 A | 11/1999 | Bao et al. |
| 6,001,130 A | 12/1999 | Bryan et al. |
| 6,022,376 A | 2/2000 | Assell et al. |
| 6,113,639 A | 9/2000 | Ray et al. |
| 6,156,067 A | 12/2000 | Bryan et al. |
| 6,234,705 B1 | 5/2001 | Troxel |
| 6,261,296 B1 | 7/2001 | Aebi et al. |
| 6,565,570 B2 | 5/2003 | Sterett et al. |

FOREIGN PATENT DOCUMENTS

| | | |
|---|---|---|
| EP | 322334 A1 | 12/1988 |
| EP | 0677277 A2 | 10/1995 |
| EP | 0767636 B1 | 4/1997 |
| EP | 1138268 | 10/2001 |
| FR | WO 90/00037 | 1/1990 |
| FR | 2681525 A1 | 3/1993 |
| FR | 2707864 A1 | 1/1995 |
| FR | 2717675 | 9/1995 |
| FR | 2722980 A1 | 2/1996 |
| FR | 2780269 A1 | 12/1999 |
| FR | 2782911 A1 | 3/2000 |
| FR | 2806614 | 9/2001 |
| FR | 2806616 | 9/2001 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

OTHER PUBLICATIONS

Waldemar Link, brochure entitled *Wirbelsäulen–Chirurgie: Instrumentarium Und Implantate Zur Wirbelsäulen–Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77–86 ©1990 Raven Press, Ltd., New York.

Richard W. Porter, MD, FRCS, FRCSE, *Spinal Stenois and Neurogenic Claudication*, SPINE vol. 21, No. 17, pp. 2046–2052, ©1996, Lippincott–Raven Publishers.

\* cited by examiner

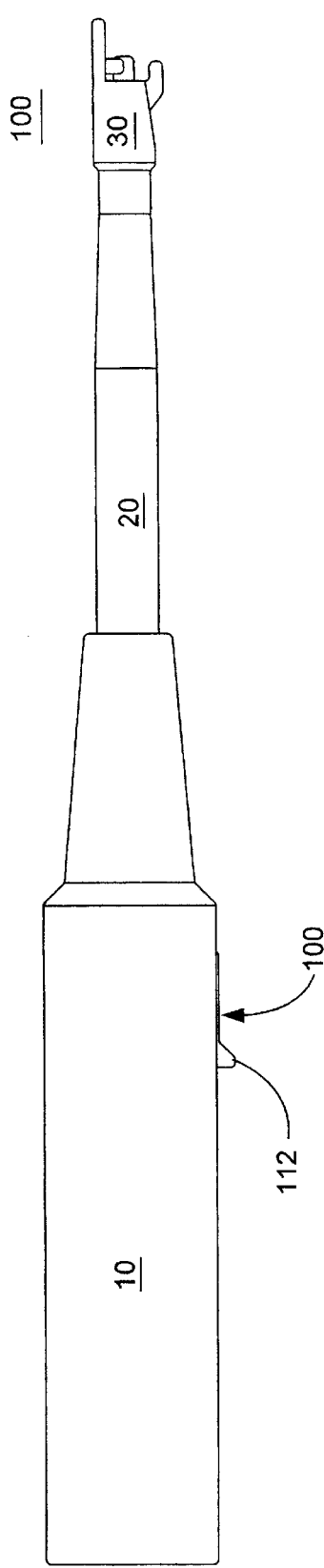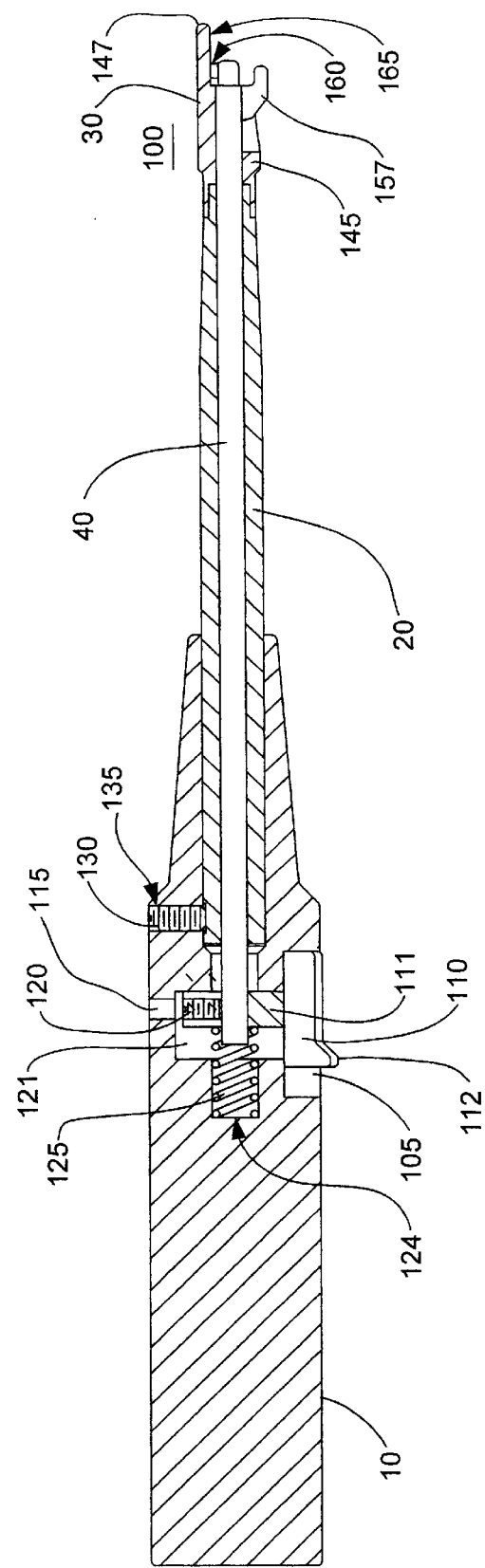

MATING INSERTION INSTRUMENTS FOR SPINAL IMPLANTS AND METHODS OF USE

RELATED CASES

This application claims priority to United States Provisional Patent Application entitled MATING INSERTION INSTRUMENTS FOR SPINAL IMPLANTS AND METHODS OF USE, filed Jul. 17, 2001, Ser. No. 60/306,101 and is a continuation-in-part of U.S. patent application Ser. No. 09/799,470 filed Mar. 5, 2001, which is a continuation-in-part of U.S. patent application Ser. No. 09/473,173 filed on Dec. 28, 1999 and entitled SPINE DISTRACTION IMPLANT, now U.S. Pat. No. 6,235,030 issued May 22, 2001, which is a continuation of U.S. patent application Ser. No. 09/179,570 filed on Oct. 27, 1998 and entitled SPINE DISTRACTION IMPLANT, now U.S. Pat. No. 6,048,342 issued Apr. 11, 2000, which is a continuation-in-part of U.S. patent application Ser. No. 09/175,645 filed on Oct. 20, 1998 and entitled SPINE DISTRACTION IMPLANT, now U.S. Pat. No. 6,068,630 issued May 30, 2000. All of the above applications and patents are incorporated herein by reference.

BACKGROUND OF THE INVENTION

1. Field of the Invention

This invention relates to instruments used for the insertion of spinal implants during spinal surgery and to the spinal implants.

2. Background of the Invention

As the present society ages, it is anticipated that there will be an increase in adverse spinal conditions which are characteristic of older people. By way of example, with aging comes increases in spinal stenosis (including but not limited to central canal and lateral stenosis), the thickening of the bones which make up the spinal column and facet arthropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

Accordingly, there needs to be developed procedures and implants for alleviating such and other spine related condition, which are minimally invasive, which can be tolerated by the elderly and for that matter any individual, and which can be performed preferably on an outpatient basis.

Additionally, there is a need to provide instruments for use with spinal implants to alleviate other spinal conditions for patients of all ages.

SUMMARY OF THE INVENTION

In general aspects, this invention is directed toward apparatus and methods for relieving pain associated with the spine. Inventive spinal implants can be inserted using inventive instruments between spinous processes using inventive methods to keep adjacent vertebrae at a desired separation.

In one series of embodiments of the invention, an implant can have a main body assembly which comprises a tissue expander, a spacer, and a main body that includes a wing. Using an embodiment of an instrument of the invention, the spacer is placed between dorsal spinous processes of adjacent vertebrae. The main body assembly has a main body wing which can be positioned on one side of adjacent dorsal spinous processes. A second, universal wing of the invention can be attached to the main body assembly and can be positioned on the other side of the adjacent dorsal spinous processes using another instrument of this invention. Upon insertion, the spacer separates the adjacent spinous processes, thereby reducing the symptoms of spinal stenosis and/or other symptoms associated with the spine. In other embodiments of the inventive spinal implant, the spacer between the wings is rotatable and can provide for placement of the implant between spinous processes.

This invention includes instruments and methods for the insertion of inventive spinal implants into the spine of a surgical patient. An insertion instrument generally has a handle for grasping and another portion which engages a portion of a spinal implant. An implant can be engaged by the insertion instrument and then can be positioned relative to adjacent vertebrae of a patient. Instruments can be desirably made of biologically inert materials, such as stainless steel, and can be designed simply, so that the component parts of the instruments can be separated easily from one another for cleaning and sterilization between uses.

In certain embodiments of the instruments of this invention, spring-actuated locking mechanisms and one or more alignment pins can unite with alignment points of the inventive implant and can hold portions of the implant. When alignment pins are present, it can be desirable to orient the longitudinal axis of the pins across the axis of the locking mechanism. When engaged by the locking mechanism and alignment pins, the implants can be held firmly in relationship to the insertion instrument, making positioning of the implant easy and convenient. When the implant is positioned and secured in place, the locking mechanism can be easily disengaged from the implant, leaving the implant in place in the spine.

In other embodiments of this invention, an insertion instrument can have a driver for engaging a fastener of a universal wing with a main body assembly, via a threaded fastener or other suitable means. When provided together, insertion instruments and implant devices can improve the efficiency of spinal surgery to relieve pain associated with spinal stenosis and other degenerative and traumatic injuries to the spine.

In yet another aspect of the invention, the insertion instrument for holding the main body can nest in the insertion instrument for holding the second or universal wing. Additionally the second wing holding insertion instrument can nest in the main body holding insertion instrument.

In still a further aspect of the invention one or both of the instrument for holding the main body and the instrument for holding the second or universal wing can have a handle provided at an angle for enhanced leverage and for mating with the other insertion instrument.

Insertion of spinal implants can be generally accomplished using three instruments of this invention, one to determine the correct size of an implant to be used and to distract the spinous processes, one to insert a main body assembly, and another to install a universal wing. After a surgical field is prepared, an incision or access port is made in the back of the patient. The intraspinous space is accessed, and specially designed trial implant instruments can be used to determine the correct size of a spinal implant to be inserted and to distract the spinous processes. Generally, the smallest trial implant is inserted between the spinous processes. If the smallest trial implant is too loose in the interspinous space, the next largest size is tried. The process continues until the correct size of implant is determined. This process can also be used, as desired, to distract apart the adjacent spinous process to a desired separation. Once the correct size of the implant is selected, a main body insertion instrument can be used to hold a main body assembly and a main body wing in position relative to the spinous processes of adjacent vertebrae. The main body assembly is urged into the intraspinous space, preferably near the vertebral body. Another instrument of this invention can be used to attach a universal wing to the main body assembly. The two wings assist in maintaining the spacer in place between the spinous processes.

BRIEF DESCRIPTION OF THE FIGURES

The invention will be described with respect to particular embodiments thereof. Other objects, features, and advantages of the invention will become apparent with reference to the specification, claims and drawings in which:

FIG. 1 depicts an exterior view of a main body insertion instrument of one embodiment of this invention for inserting an implant body into the spine of a patient.

FIG. 2 depicts a schematic, sectional, longitudinal view of a main body insertion instrument as depicted in FIG. 1.

FIGS. 3a–3c depict the following.

FIG. 3a depicts a side view of the insertion tip of a main body insertion instrument of one embodiment of this invention with a locking pin and spacer engagement pin spacer in the extended position.

FIG. 3b depicts the insertion tip as shown in FIG. 3a with a locking pin and spacer engagement pin spacer in a retracted position.

FIG. 3c depicts a top view of the insertion tip of the main body insertion instrument of one embodiment of this invention with the locking pin and engagement pin spacer in a retracted position.

FIGS. 9a–9c depict the following.

FIG. 9a is a side view showing the relationships of an embodiment a universal wing of the invention and an embodiment of a wing insertion instrument of the invention, showing the points of engagement.

FIG. 9b is a side view of the embodiment of the universal wing and the wing insertion instrument of the invention depicted in FIG. 9a after engagement.

FIG. 9c is a top view of the embodiment of a universal wing and a wing insertion instrument of the invention as depicted in FIG. 9b.

FIGS. 11a and 11b depict the following.

FIG. 11a depicts a lateral view of a spine, and an embodiment of a main body insertion instrument of the invention engaged with an embodiment of a main body assembly of the invention positioned between spinous processes of adjacent vertebrae of a patient.

FIG. 11b depicts a dorsal view of a spine of a patient depicting an embodiment of a main body assembly of the invention inserted between spinal processes of adjacent vertebrae.

DETAILED DESCRIPTION OF THE INVENTION

Figure 3A:
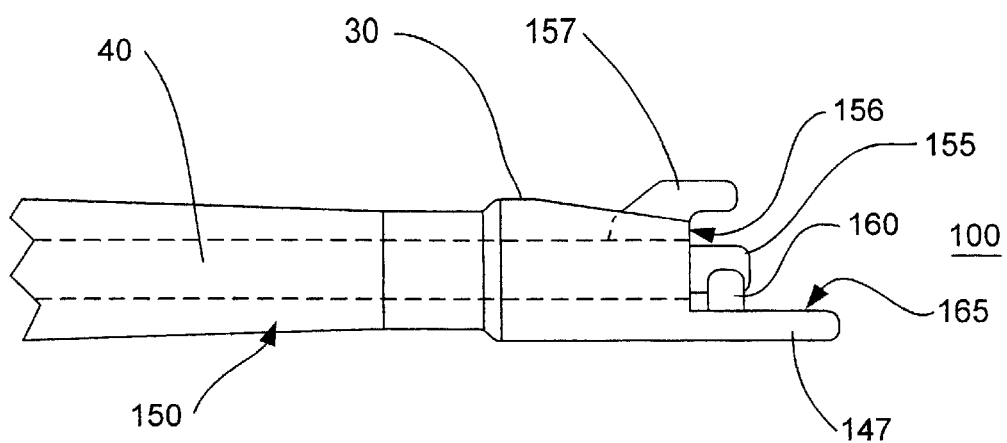
FIGS. 3a–3c depict schematic views of an insertion tip of the main body insertion instrument of one embodiment of this invention as shown in FIGS. 1 and 2. More particularly.

This invention includes instruments and methods for inserting spinal implants in the vertebral columns of patients and to spinal implants themselves. In one embodiment, instruments are provided for inserting a main body assembly between spinous processes of adjacent vertebrae. These instruments, termed herein "main body insertion instruments" generally comprise an elongated body portion having a handle at one end, an insertion shaft and an insertion tip. The insertion tip engages with the main body assembly and holds the assembly in fixed relation to the instrument. The surgeon prepares the site for implantation, and uses the instrument to urge the assembly between spinous processes of adjacent vertebrae.

In other embodiments of this invention, different instruments can be used to insert universal wings on to the main body assembly of the spinal implant. These other instruments are termed herein "wing insertion instruments." A wing insertion instrument generally comprises a handle, an insertion shaft and an insertion tip. The insertion tip of a wing insertion instrument engages with the universal wing and holds it fixed relative to the instrument. The surgeon then grasps the handle portion of the instrument and uses it to urge the wing implant portion into proximity with a main body assembly which has been inserted between spinous processes of the spine.

I. Main Body Insertion Instrument

Main body insertion instrument of this invention is illustrated, by way of example only, in FIGS. 1–3. FIG. 1 depicts an exterior view of a main body insertion instrument 100 of this invention having a handle 10, an insertion shaft 20 and an insertion tip 30. Handle 10 can be made of any suitable material, such as by way of example only, Gray ULTEM™, a polyetherimide resin. Insertion shaft 20 can be made of any suitable, strong material, such as 304 stainless steel. Insertion shaft 20 has a central bore extending through its length. The proximal end of insertion shaft 20 is adapted to fit within the distal end of handle 10, and can be held in place with a set screw, made of, by way of example only, 304 or 455 stainless steel. A main body insertion tip 30 is attached to the distal end of the insertion shaft. Insertion tip 30 can be made of, by way of example only, 17-4 stainless steel. A bore extends longitudinally through the insertion tip 30 and is contiguous with the bore through the insertion shaft 20. An insertion rod 40, having a distal end with a spacer engagement pin and a locking pin, extends through the length of the bore in insertion shaft 20. Insertion rod 40 extends into the handle 10 of the main body insertion instrument 100. On one side of handle 10, insertion knob 110, having a raised portion 112, is for manipulation of a locking pin and spacer engagement pin in insertion tip 30. The insertion knob 110 can be made of, by way of example only, 304 stainless steel. The stainless steel components of the instruments of this invention can desirably meet ASTM Standard F899-95: Standard Specifications for Stainless Steel Billet, Bar, and Wire for Surgical Instruments.

FIG. 2 depicts a longitudinal cross-sectional view of a main body insertion instrument 100 as depicted in FIG. 1, and shows details of this embodiment of the invention. Handle 10 has an insertion knob groove 105 on a lateral surface, within which insertion knob 110 is provided. Insertion knob 110 and groove 105 are sized so that insertion knob 110 can move in a proximal/distal path along the handle 10. Insertion knob 110 has said raised portion 112 used for applying force to move insertion knob 110 proximally and distally along handle 10. Insertion knob 110 is attached to rod 111, which is located within cavity 121 of the cavity 121. When placed within cavity 121, the rod 111 engages spring 125, which is located within an interior space 124 of handle 10. Spring 125 is urged against insertion rod 40. The spring provides a force that urges rod 111 and also rod 40 toward the distal portion of the instrument 100. Spring 125 is compressed by manual movement of insertion knob 110 in a proximal direction, acting via rod 111. Because insertion rod 40 is engaged with rod 111, insertion rod 40 is drawn proximally by proximal movement of insertion knob 110. When manual force on insertion knob 110 is relaxed, as for example, after alignment of a main body implant in relation to insertion tip 30, spring 125 urges rod 111, insertion rod 40 and insertion knob 110 in a distal direction. As insertion rod 40 is urged distally, locking pin 155 and spacer engagement pin 157 are urged toward the distal end of insertion instrument 100 as well, where pins 155, 157 can engage the main body assembly of the spinal implant. FIG. 2 depicts insertion shaft 20 having a proximal end that is adapted to fit within the distal portion of handle 10. When so placed, set screw 130 engages with insertion shaft 20 to keep insertion shaft 20 engaged in handle 10. Set screw 130 can be made of any convenient material, such as, by way of example only, stainless steel. It can be especially desirable for set screws 120 and 130 to be completely removable from handle 10, to provide open access to the interior of handle 10 for cleaning and sterilization.

Insertion tip 30 is adapted to fit onto the distal end of insertion shaft 20, by way of example only, with an interference fit. FIG. 2 depicts such an interference fit engagement of insertion tip 30 with the distal end of insertion shaft 20. However, other ways of attaching insertion tip 30 to insertion shaft 20 are contemplated and are considered to be part of this invention.

FIG. 2 depicts components of insertion tip 30, which include a proximal portion 145, which can act as a position stop for spacer engagement pin 157. Spacer engagement pin 157 protrudes laterally from the portion of the insertion rod 40, and is adapted to engage a spacer engagement hole of a main body assembly. When so engaged, spacer engagement pin 157 can position a spacer relative to the remainder of the main body wing and tissue expander, making insertion of the implant between spinous processes convenient. At the distal end of insertion rod 40, locking pin 155 is positioned to engage a hole in the main body assembly. Thus, when so engaged, locking pin 155 and spacer engagement pin 157 can hold the main body, tissue expander and spacer in position relative to one another for convenient insertion. At the distal end of the insertion tip 30, portion 147, having a flat medial surface 165, can support the main body. In some embodiments, one or more alignment pins 160 can be provided to engage with a main body to provide additional support during surgery.

In general, the construction of main body insertion instrument 100 desirably is sufficiently robust to provide firm support of the main body assembly during surgery. For example, in certain situations, it can be desirable for the surgeon to exert relatively large forces on the main body assembly to urge the tissue expander between spinous processes. Generally, the connective tissue, including ligaments, can be strong and tough, tending to resist stretching. However, during surgery using the spinal implants and insertion instruments of this invention, it may be desirable to deflect, distract and/or stretch the ligaments to permit passage and proper location of spinal implants. In these situations, the instruments are strong and rigid.

It also can be desirable for the surfaces to be smooth and have relatively simple geometrical shape. Simple shape and relatively open construction can provide for easy access to the interior of the parts of the instrument, and can permit easy and convenient cleaning and sterilization.

Figure 3B:
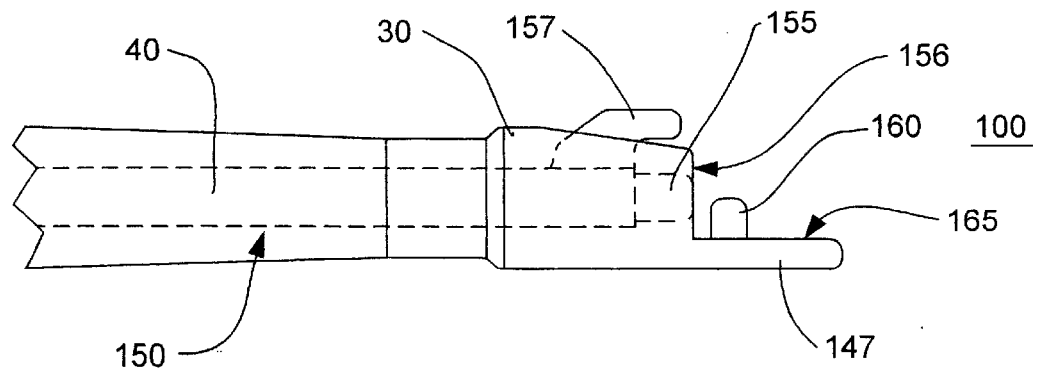
Figure 3C:
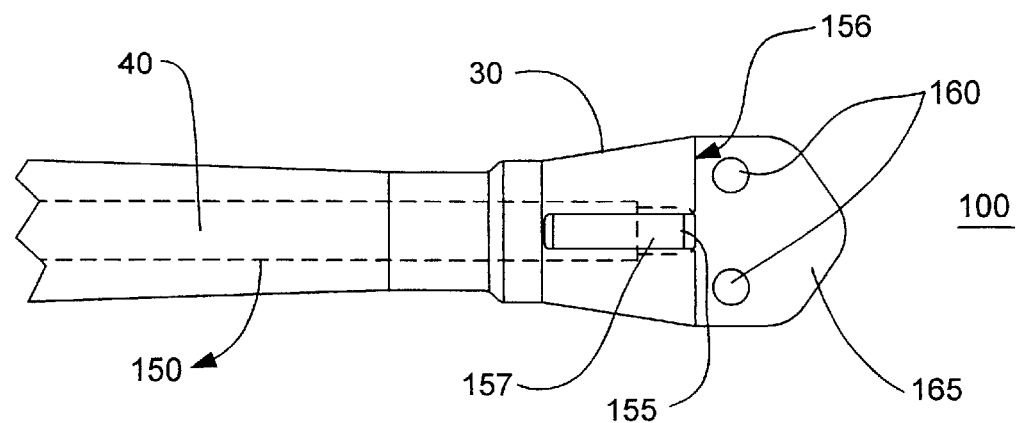

FIGS. 3a–3c depict the insertion tip 30 of main body implant insertion instrument 100 in additional detail. FIG.

3a depicts a side view of insertion tip 30 fitted into the distal end of insertion shaft 20. Bore 150 of insertion shaft 20 is shown in dashed lines. Locking pin 155 of insertion rod 40 is shown in the distal-most extension, as urged by spring 125 of FIG. 2. Portion 147 is shown having alignment pin 160 with an axis aligned substantially perpendicularly to the plane of portion 147. Spacer engagement pin or catch 157 is shown above locking pin 155. At its distal-most extension, locking pin 155 crosses the axis of alignment pin 160. When alignment pin 160 and spacer engagement pin 157 have engaged their respective portions of a main body assembly, the assembly can be firmly held by the insertion tip 30.

FIG. 3b depicts an insertion tip as shown in FIG. 3a in which the insertion rod 40 has been moved to a proximal position. In the embodiment depicted in FIG. 3b, locking pin 155 and spacer engagement pin 157 have been retracted sufficiently to be proximal to surface 156 of insertion tip 30. When so positioned, the main body assembly can be disengaged from insertion tip 30 and the instrument can be withdrawn from the patient's body, leaving the main body assembly in place.

FIG. 3c depicts a top view of insertion tip 30. Insertion rod 40 is shown in the retracted position, with locking pin 155 and spacer engagement pin 157 being located proximally to surface 156 of insertion tip 30. Two alignment pins 160 are shown. When engaged with a main body assembly, flat surfaces 156 and 165, alignment pins 160, and locking pin 155 and spacer engagement pin 157 of the instrument 100 can hold the main body assembly firmly to the insertion instrument.

Figure 4A:
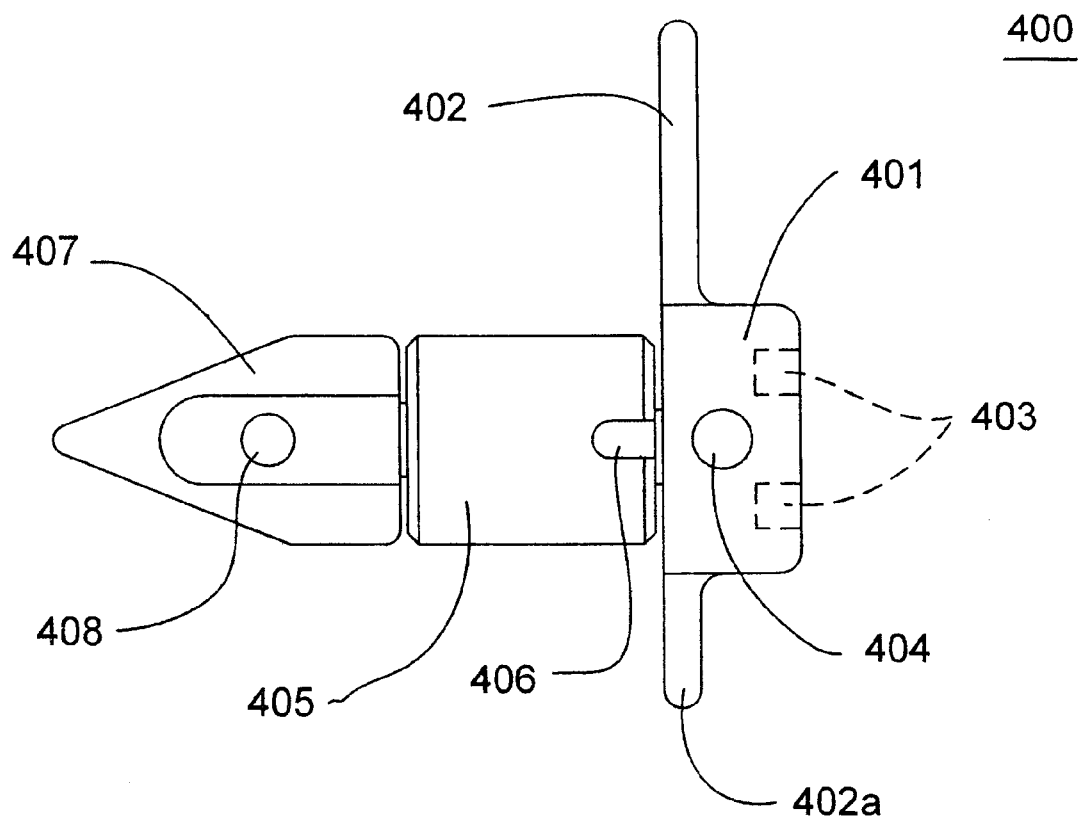
FIG. 4a depicts an embodiment of a main body assembly of a spinal implant of the invention used with a main body insertion instrument of this invention.
Figure 4B:
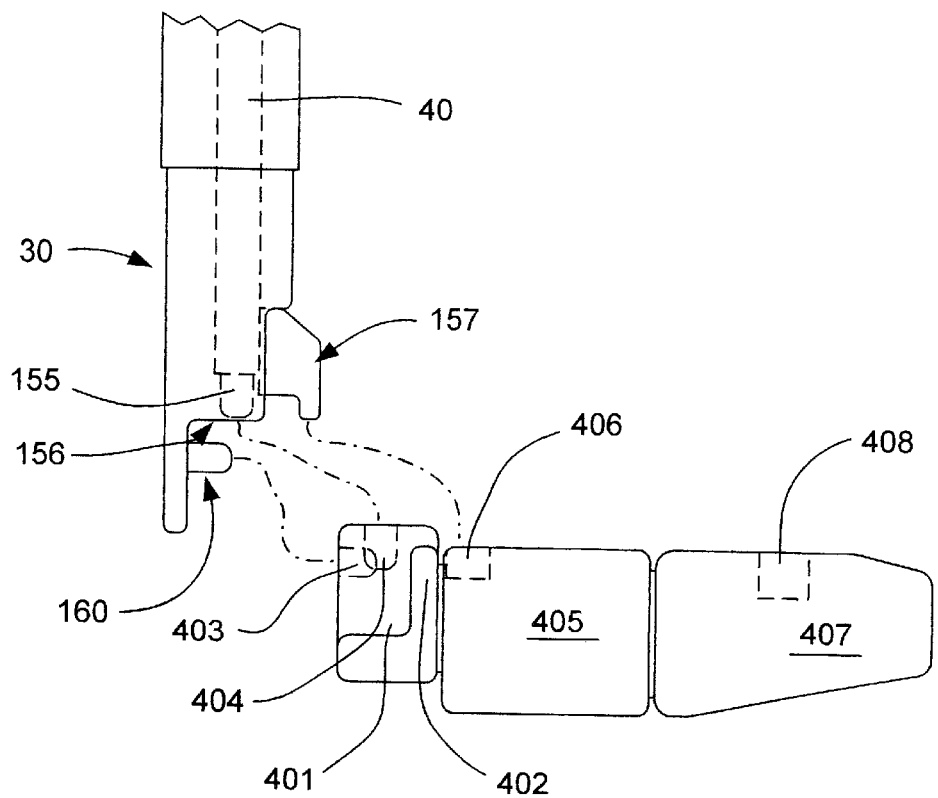
FIG. 4b depicts an embodiment of a main body insertion instrument of this invention and an embodiment of a main body assembly of the invention as shown in FIG. 4a, showing the points of engagement between the assembly and the instrument.
Figure 4C:
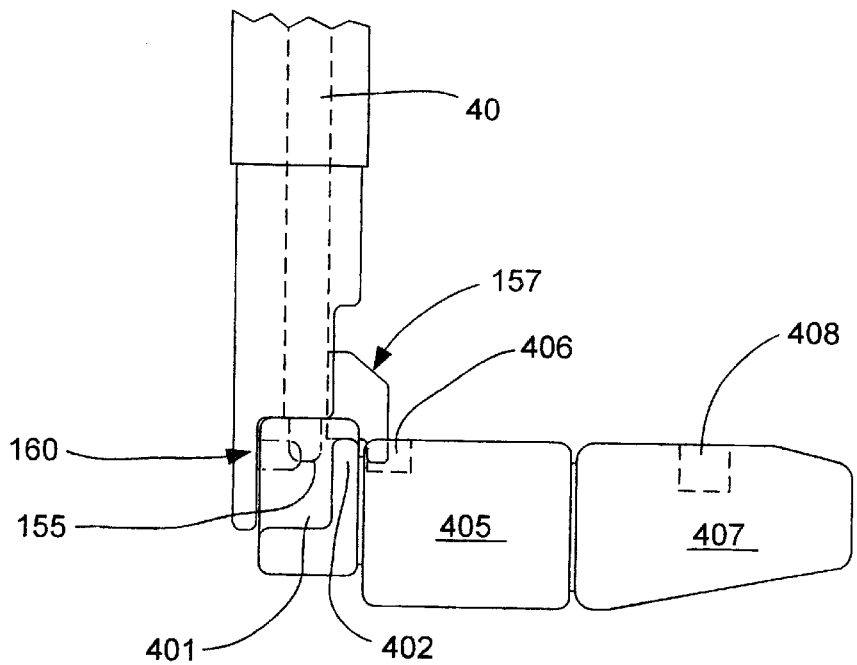
FIG. 4c depicts an embodiment of a main body assembly of the invention and an embodiment of a main body insertion instrument of the invention, both depicted in FIG. 4b, engaged with one another.

FIGS. 4a–4c depict the method of engagement of a main body insertion instrument of the invention with a main body assembly of the invention.

FIG. 4a depicts a main body assembly 400 of the invention for use with the instrument 100 of this invention. Main body assembly 400 has a main body wing 401 having a cephalad wing member 402 and a caudal wing member 402a. Cephalad wing member 402, after insertion, is aligned toward the head of the subject along the right side of a dorsal spinous process. Member 402a is also positioned along the side of a spinous process. Main body wing 401 also can have one or more holes 403 adapted to receive alignment pins 160 of main body insertion instrument 100. Main body wing 401 also has locking pin hole 404 adapted to receive locking pin 155 of main body insertion instrument 100. Main body wing 401 is attached to spacer 405, which has spacer engagement hole 406 adapted to receive spacer engagement pin 157 of insertion instrument 100. On the other end of spacer 405, tissue expander 407 is shown, having a threaded hole 408 adapted to receive a bolt of a universal wing implant (described below). Tissue expander 407 has a tapered left end to ease insertion of the main body assembly between spinous processes.

FIG. 4b depicts a lateral view showing the points of engagement between a main body assembly and main body insertion instrument. Insertion rod 40 of insertion instrument is shown in a retracted, or proximal position. Locking pin 155 and spacer engagement pin 157 are shown aligned proximally to plane 156 of insertion tip 30. Spacer engagement pin 157 is adapted to engage with spacer engagement hole 406, locking pin 155 is adapted to engage with locking pin hole 404, and alignment pin 160 is adapted to engage with alignment hole 403.

FIG. 4c depicts main body insertion instrument engaged with main body assembly. While insertion rod 40, locking pin 155 and spacer engagement pin 157 are in the retracted position, a main body assembly has been positioned with alignment pin 160 received into alignment pin hole 403. Thereafter, insertion rod 40 has been urged distally by the spring 125 of FIG. 2, thereby engaging locking pin 155 with locking pin hole 404 and spacer engagement pin 157 with spacer engagement hole 406. The engagement of spacer engagement pin 157 with spacer 405 keeps spacer 405 from rotating about its axis, and thereby keeps the spacer 405 in position relative to the tissue expander 407 and to the main body implant insertion instrument 100.

II. Wing Insertion Instrument

Figure 5:
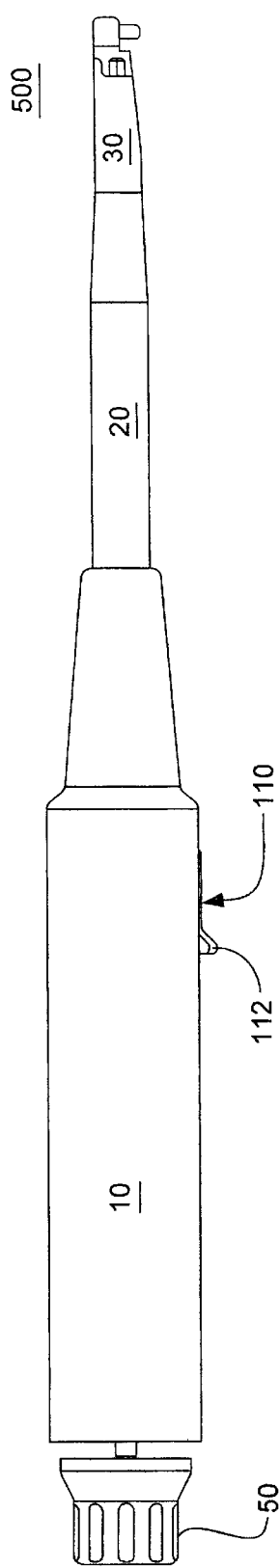
FIG. 5 depicts an exterior view of an embodiment of a wing insertion instrument of the invention.
Figure 6:
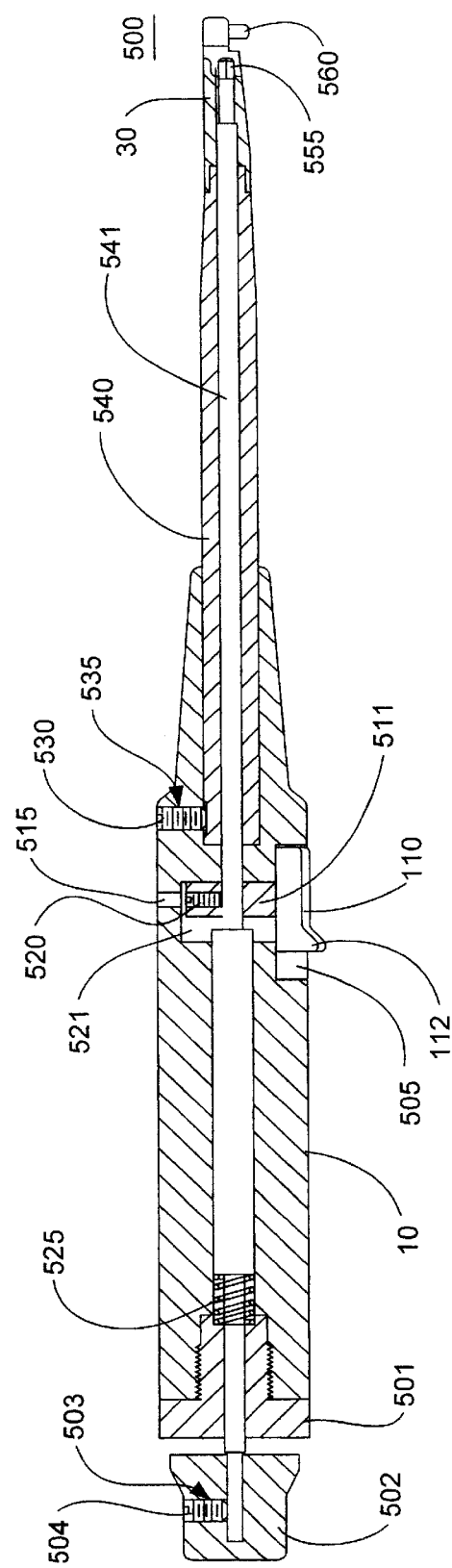
FIG. 6 depicts a schematic, sectioned, longitudinal view of the embodiment of a wing insertion instrument of the invention as shown in FIG. 6.

A wing insertion instrument of this invention is depicted in FIGS. 5–7. FIG. 5 depicts an exterior, lateral view of a wing insertion instrument 500, having a handle 10, and insertion shaft 20, an insertion tip 30 and a driver knob 50. As with the main body insertion instrument 100 depicted in FIGS. 1 and 2, on a lateral surface, insertion knob 110, having raised portion 112 is provided to actuate a locking mechanism at the distal end of the instrument.

FIG. 5 depicts a cross-sectional longitudinal view through the wing insertion instrument 500 of this invention. Handle 10 has an insertion knob groove 505 on a lateral surface, within which insertion knob 110 is provided. Insertion knob 110 and groove 505 are sized so that insertion knob 110 can move in a proximal/distal path along the handle 10. Insertion knob 110 has a raised portion 112 used for applying force to move insertion knob 110 proximally and distally along handle 10. Insertion knob 110 is attached to rod 511, which is located within interior space 521 of the handle 10. Rod 511 engages insertion rod 541 by way of set screw 520 which is accessible through hole 515. Hole 515 is desirably of sufficient size to permit complete removal of set screw 520 from the instrument, permitting insertion knob 110 to be removed from handle 10 and the instrument to be cleaned and sterilized.

Insertion shaft 540 has a proximal end that fits within the distal portion of the bore of handle 10. Set screw 530 is inserted through hole 535, and engages insertion shaft 540 with handle 10. It is desirable for hole 535 to be of sufficient size for set screw 530 to be completely removed, permitting cleaning and sterilization of the component parts of instrument 500.

Insertion rod 541 extends through the full length of the bore of instrument 500, and has a proximal portion sized to accommodate spring 525. When installed in handle 10, insertion rod 541 compresses spring 525. The distal end of spring 525 is held in place by handle end cap 501, which, along with handle 10 can be made of by way of example, Gray ULTEM™. Handle end cap 501 is engaged with handle 10 by means of threads. Thus, for disassembly, handle end cap 501 can be disengaged from handle 10, and spring 525 and insertion rod 541 can be removed from the proximal end of handle 10. When assembled, rod 511 and insertion knob 110 are urged by spring 525 in a distal direction. The distal motion is stopped when insertion knob 110 or rod 511 reach the distal wall of space 521. Spring 525 is further compressed by manual movement of insertion knob 110 in a proximal direction, acting via insertion rod 511. Because insertion rod 541 is engaged with rod 511, insertion rod 541 is drawn proximally by proximal movement of insertion knob 110. When manual force on insertion knob 110 is relaxed, as for example, after alignment of a universal wing in relation to insertion tip 30, spring 525 urges insertion rod 541 and insertion knob 110 in a distal direction. As insertion rod 541 is urged distally, driver 555 is urged toward the distal end of insertion instrument 500 as well.

Driver knob 502 is provided at the proximal end of instrument 500. Driver knob 502 can be made of, by way of example, Gray ULTEM™. Driver knob 502 has a bore into which the proximal most extension of insertion rod 541 is placed. Insertion rod 541 is held within driver knob 502 by means of set screw 504 within hole 503. It can be desirable for hole 503 to be sufficiently large so that set screw 504 can be completely removed from driver knob 502 for cleaning and sterilization. Insertion rod 541 desirably is free to rotate about its longitudinal axis, so that when driver knob 504 is rotated, driver 555 is rotated.

In summary and referring to FIGS. 2 and 6, set screws 120, 130 of main body insertion instrument 100, and set screws 520, 530, and 504 of universal wing insertion instrument 500 can be removed using a hex screw driver, having a hexagonal driver head made of, by way of example, 455 stainless steel. Such removal can be used to disassemble the instruments 100 and 500 for cleaning.

Figure 7A:
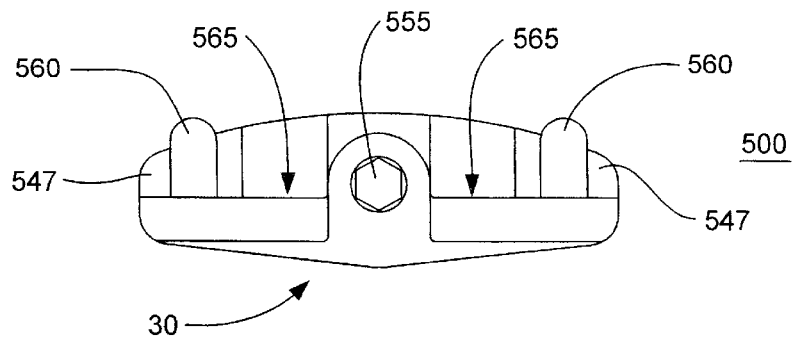
FIG. 7a depicts an end view of an embodiment of an insertion tip of a wing insertion instrument of the invention are depicted in FIGS. 5 and 6.
Figures 7B, 7C:
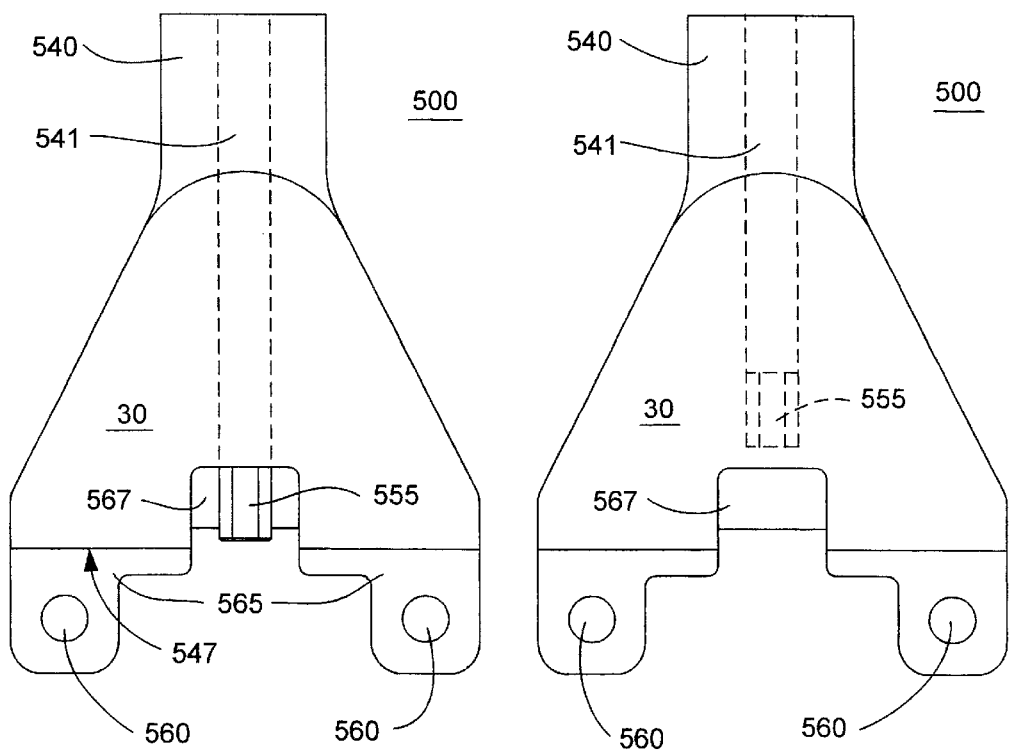
FIG. 7b depicts a top view of an embodiment of an insertion tip of a wing insertion instrument of the invention as depicted in FIG. 7a with a driver in a distal position.
FIG. 7c depicts a top view of the embodiment of the insertion tip of a wing insertion instrument of the invention as depicted in FIGS. 7a and 7b with the driver in a proximal position.

FIGS. 7a–7c depict details of insertion tip 30 of wing insertion instrument 500 of this invention. FIG. 7a is an end-view of the distal end of insertion tip 30, showing driver 555, alignment pins 560, and surfaces 547 and 565. An edge of universal wing 800 can abut surface 547 to provide support during the insertion of universal wing 800. A surface of universal wing 800 can abut surface 565 to provide additional support of universal wing 800.

FIG. 7b depicts a bottom view of insertion tip 30 of wing insertion instrument 500. Insertion rod 541 is depicted in a distal position, within insertion shaft 540. Driver 555 is shown extending into space 567 of insertion tip 30. FIG. 7c depicts a bottom view of the insertion tip 30 as shown in FIG. 7b with the driver 555 and insertion rod 541 in a proximal position, with the distal-most end of driver 555 retracted from the space 567. In this position, mounting ring 816 of FIG. 8 (below) of a universal wing can be received in space 567.

Figure 8A:
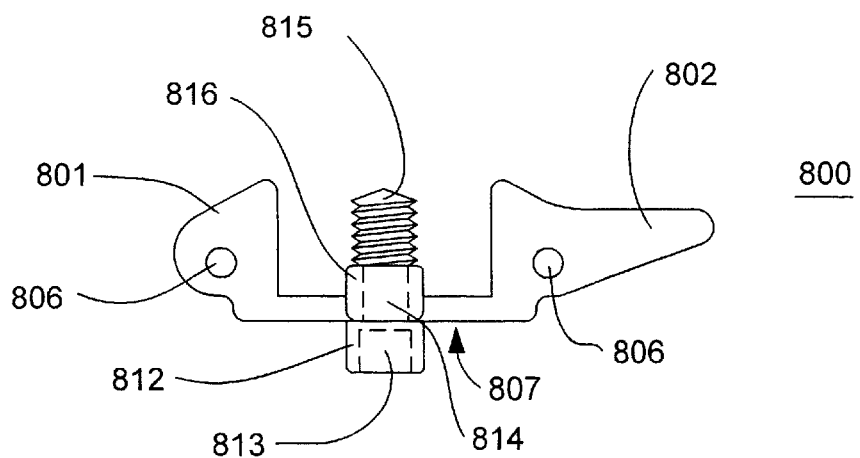
FIG. 8a depicts a side view of an embodiment of a universal wing of the invention which is implantable with a wing insertion instrument of the invention.
Figure 8B:
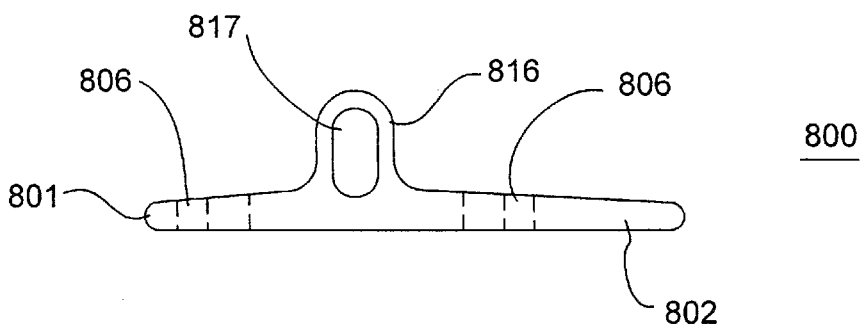
FIG. 8b depicts an end view of an embodiment of a universal wing of the invention are depicted in FIG. 8a without an attachment bolt.
Figure 8C:
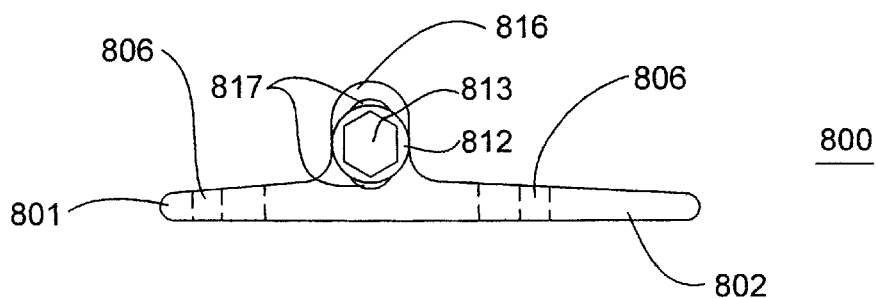
FIG. 8c depicts the embodiment of an embodiment of the universal wing of the invention as shown in FIG. 8b with an attachment bolt.

FIGS. 8a–8c depict a universal wing 800 of the invention for use with the wing insertion instrument 500 of the invention. FIG. 8a is a lateral view of universal wing 800, having caudad portion 801 and cephalad portion 802. Alignment holes 806 are adapted to receive alignment pins 560 of wing insertion instrument 500. Although two alignment holes 806 are depicted, additional or fewer alignment holes can be provided. Between caudad portion 801 and cephalad portion 802, mounting ring 816 is provided having an oblong bore therethrough to receive shaft 814 of bolt 812. Bolt 812 has a proximal end with a recess 813 adapted to receive driver 555 of instrument 500. The distal end of bolt 812 is threaded to engage with hole 408 of a tissue expander 407 depicted in FIGS. 4a–4c. The oblong bore has partial threads that allow a bolt to be screwed through the bore with the smooth shaft of the bolt then trapped in the bore.

FIG. 8b is a side view of universal wing 800 without bolt 812, depicting mounting ring 816 with oblong bore 817 therethrough. Alignment holes 806 are shown as dashed lines. FIG. 8c depicts a similar view of universal with 800 with bolt 812 provided. Hex recess 813, adapted to receive driver 555 of instrument 500 is shown. Hole 817 is oblong to provide a choice of positions of bolt 812 within bore 817. By providing a choice of bolt positions, the surgeon can install universal wing with a desired spacing between universal wing 800 and main body wing 401.

Figure 9A:
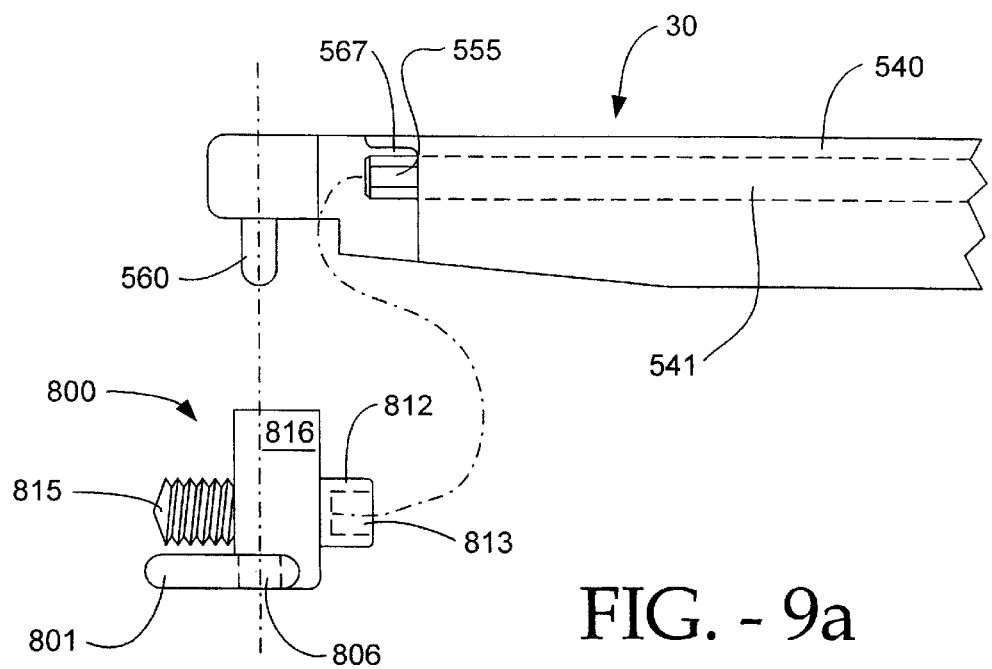
FIGS. 9a–9c depict an embodiment of an insertion tip of a wing insertion instrument of the invention as shown in FIGS. 6 and 7, and an embodiment of a universal wing of the invention. More particularly.
Figure 9B:
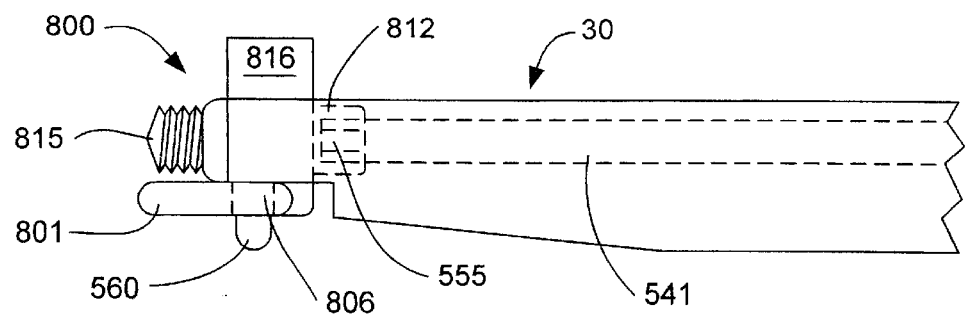
Figure 9C:
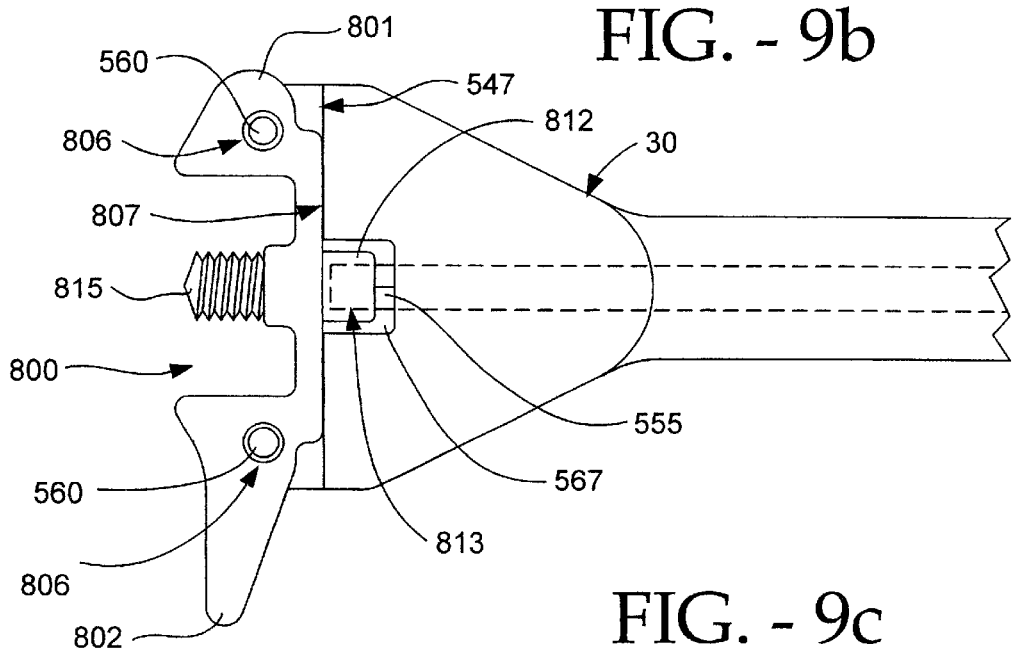
Figure 10:
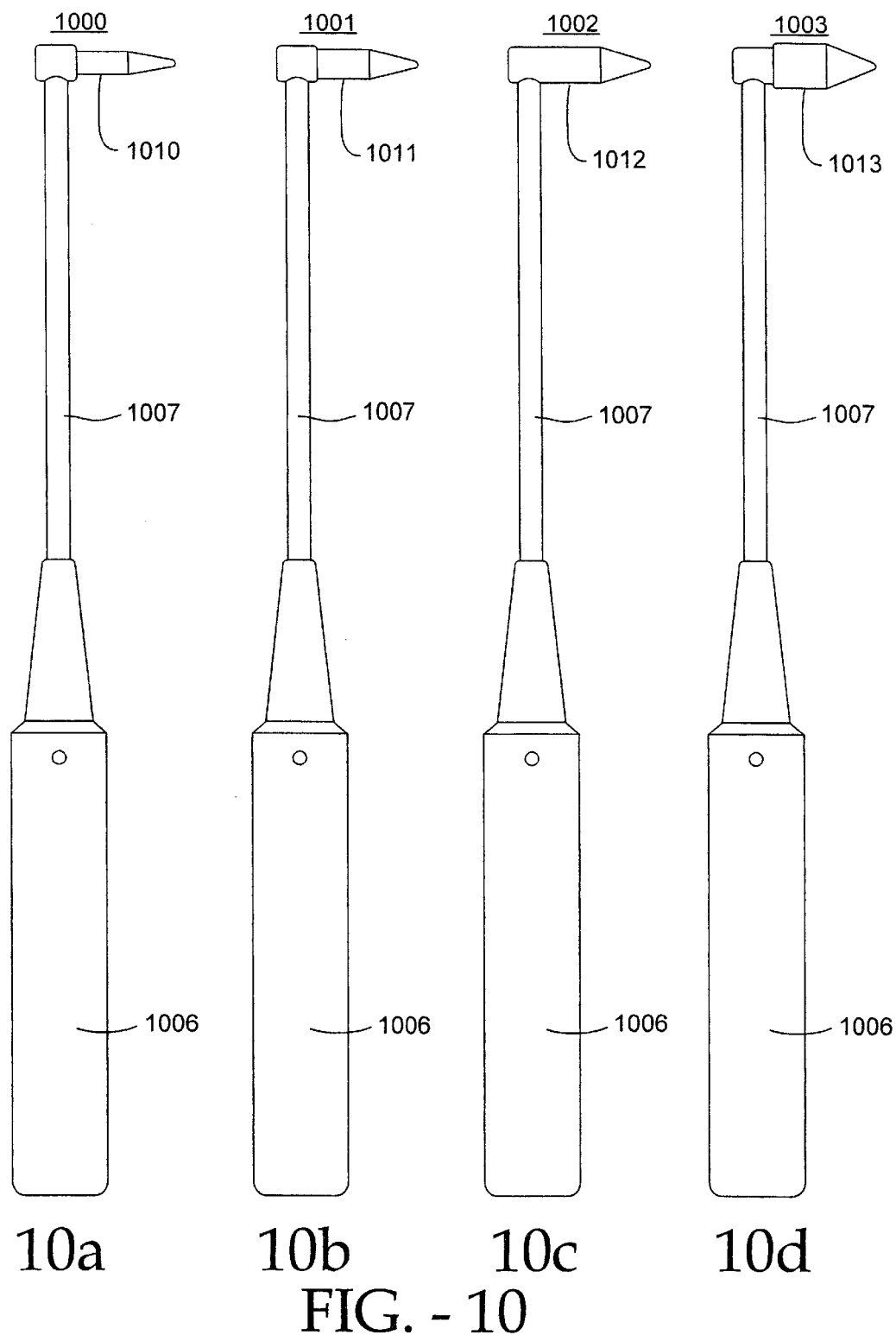
FIGS. 10a–10d depict trial implantation and distraction instruments of the invention.

FIGS. 9a–9c depict the relationships between wing insertion instrument 500 of this invention and the universal wing 800 of the invention. FIG. 9a depicts a lateral view of the insertion tip 30, with driver 555 in space 567 and alignment pin 560. Insertion rod 541 is shown within insertion shaft 540. Also depicted is universal wing 800, having bolt 812 with recess 813, mounting ring 816, alignment hole 806, and caudad wing portion 801. The axes of driver 555 and alignment pin 560, which in this embodiment cross each other and can be substantially perpendicular if desired, are shown in relation to recess 813 and alignment hole 806, respectively.

FIG. 9b depicts a lateral view of insertion tip 30 engaged with universal wing 800. Driver 555 is received by recess 813 in bolt 812 and alignment pin 560 is received by alignment hole 806. Bolt 812 is received within recess 567 of insertion tip 30, and when insertion shaft 541 is rotated, bolt 812 can rotate.

FIG. 9c depicts a bottom view of insertion tip 30 and universal wing 800, engaged as in FIG. 9b. Cephalad portion 802 and caudad portion 801 of the universal wing are shown engaged by alignment pins 560 received through alignment holes 806. Edge 807 of wing 800 is shown abutted against surface 547 of insertion tip 30.

III. Trial Implant Instruments

Spinal implant surgery can be carried out by using specially designed instruments to determine the correct size of an implant to be used and to predistract the spinous process. The instruments incorporating trial implants comprise a handle, made of a convenient material, for example, Gray ULTEM™. FIGS. 10a–10d depict four embodiments of trial implant instruments of the invention. FIGS. 10a–10d depict instruments 1000, 1001, 1002, and 1003 of this invention, each having handle 1006 and insertion shaft 1007. The instruments differ in the size of the trial implant for each. Trial implant 1010 is the smallest, implant 1011, 1012, and 1013 become progressively larger, corresponding to instruments 1000, 1001, 1002 and 1003, respectively. These trial implants in the embodiment are cylindrical in shape with diameters of 6 mm, 8 mm, 10 mm, and 12 mm, respectively. The trial implants have a lead-in nose, guide, or tissue expander that is cone shaped. Other shapes such as elliptical shapes, oval shapes, and egg-shapes are within the scope of the invention. Further, the nose can be of other shapes such as pyramid shaped. In use, these trial implant instruments are used one after the other to size the implant location and to progressively distract the implant location in preparation for insertion of the implant, which is left in the patient.

IV. Methods of Insertion of Spinal Implants

To use the instruments of this invention to insert spinal implants of the invention, a patient is placed, desirably in a lateral decubitus position with maximum flexion of the lumbar spine. Lateral decubitus position permits easy orientation of the main body assembly during surgery. Generally, the implant can be inserted between the spinous processes from the bottom or right side of the spinous processes to the top or left side of the spinous processes. Such orientation permits easy visualization of the main body assembly when the universal wing is attached. The wings should be oriented properly, with cephalad portions 402 and 802 oriented in a cephalad direction, and caudad portions 402a and 801 oriented in a caudal direction. The field is prepared for sterile surgery, and local anesthesia of the area is provided. Once the entry point is determined, local anaesthetic is applied to the skin and the underlying musculature.

To insert a spinal implant in one affected vertebral area for a single level implant process, a midline incision about 1.5 inches long is made at the entry point, exposing the supraspinous ligament overlying the spinous processes at the symptomatic level. The fascia may be incised on either side of the spinous processes and supraspinous ligament. The paraspinous musculature can be elevated laterally from both sides of the midline. The supraspinous ligament is desirably preserved. The interspinous ligament may be separated to permit insertion of main body assembly 400.

To insert spinal implants in adjacent portions of the spine for a double level implant process, a midline incision about 3 inches long is made at the entry point, exposing the supraspinous ligament overlying the spinous processes at the appropriate segments. The fascia is incised if necessary on either side of the spinous processes and supraspinous ligament. The paraspinous musculature can be elevated laterally from both sides of the midline.

The first implant 400 can be inserted at the inferior level, and the second implant 400 of the same or different size, can be inserted at the superior, adjacent level after the first implant has been completely secured. If the supraspinous ligament is compromised during the procedure, it can be desirable to suture the excision in the ligament closed after insertion of the spinal implant.

Before installing the spinal implant 400, the intraspinous space is prepared using trial implants. Generally, the surgeon can first select the smallest trial implant, for example, trial implant 1000. The trial implant 1000 is urged between the spinous processes of the patient, and if little resistance is encountered, the surgeon can select a larger sized trial implant, such as trial implant 1001. If insufficient resistance is encountered, the surgeon can use progressively larger trial implants to distract the spinous process. When the correct trial implant is found, the spinal implant 400 is then chosen for insertion. Additionally, the surgeon may choose to use a trial implant instrument that is larger than the implant to be used in order to further distract the spinous process to make the insertion of the implant easier.

To insert the main body assembly, a surgeon or assistant engages such assembly with main body insertion instrument 100 of this invention. The leading edge of tissue expander 407 of the main body assembly is advanced through the interspinous ligament. If significant resistance is encountered during the insertion of the implant, the next smallest size main body assembly can be used. Once the correct sized implant has been selected, the main body implant is inserted as shown in FIGS. 11*a* and 11*b*.

Figure 11A:
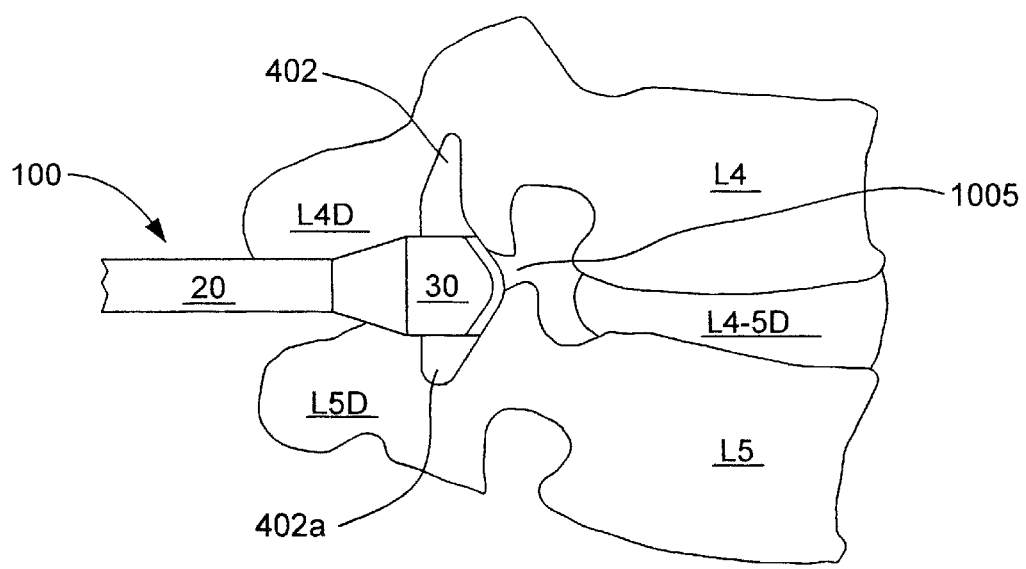
FIGS. 11a and 11b depict the insertion of a main body assembly of the invention into the spine of a patient. More particularly.

FIG. 11*a* depicts a right lateral view of a portion of a spine of a patient. L4 and L5 refer to lumbar vertebrae 4 and 5, respectively. For purposes of illustration only, these lumbar segments are depicted. However, any spinal segments can be the sites of insertion of the implants by use of the instruments of this invention. L4–5D refers to the intravertebral disk. L4D and L5D refer to the dorsal spinous processes of L4 and L5, respectively. Main body insertion instrument 100 having insertion tip 30 attached to main body assembly 400 is shown in position. Cephalad portion 402 and caudad portion 402*a* of a main body wing are shown. It can be desirable to urge main body assembly 400 ventrally within intraspinous space 1005.

Figure 11B:
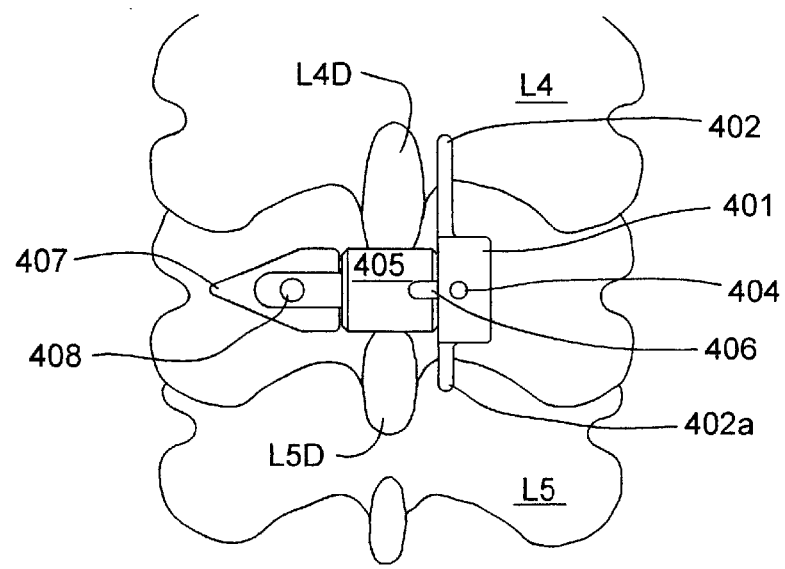

FIG. 11*b* depicts a dorsal view of an inserted main body assembly 400. Spacer 405 is shown between dorsal spinous processes L4D and L5D. Main body wing 401 is shown near the right lateral surfaces of spinous processes L4D and L5D.

Figure 12:
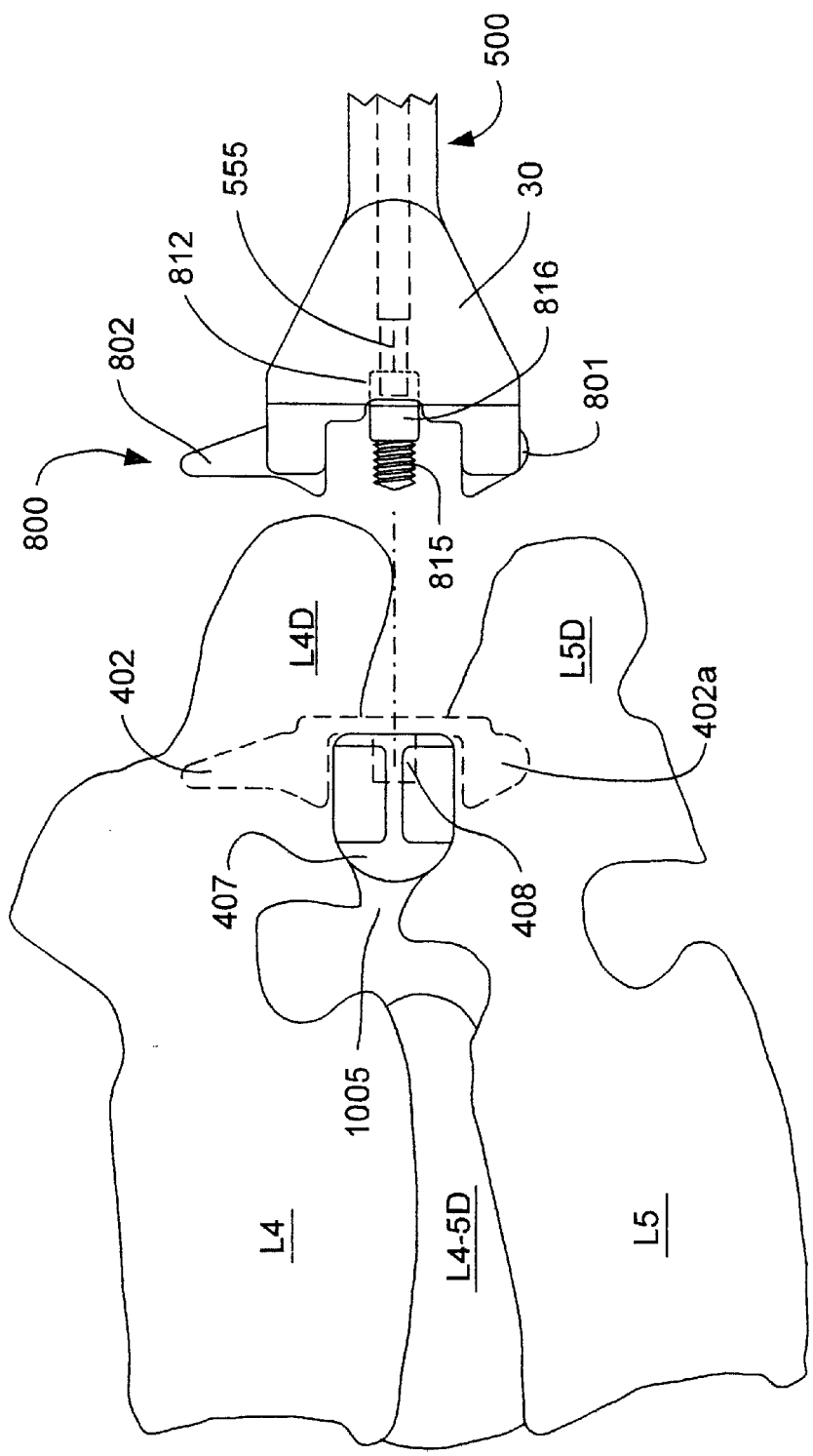
FIG. 12 depicts a lateral view of a spine with an embodiment of a main body assembly of the invention inserted between spinous processes of adjacent vertebrae and a wing implant insertion instrument of the invention engaged with an embodiment of a universal wing of the invention, showing the points of attachment between the embodiment of the main body assembly and the universal wing of the invention.

FIG. 12 depicts a left lateral view of the L4–L5 area of a patient. The main body assembly 400 has been inserted, and the tissue expander 407 is shown, urged ventrally in intraspinous space 1005. Main body wing portions 402 and 402*a* are shown in dashed lines, being located behind (i.e., the right of) the spinous process L4D and L5D, respectively. Threaded hole 408 in tissue expander 407 is shown, and axis (dashed lines) is shown to depict the insertion of threaded portion 815 of bolt 812 of universal wing 800. Insertion tip 30 of wing insertion instrument 500 is shown, with a universal wing engaged 800, as depicted in FIGS. 9*b* and 9*c*. The engaged wing is shown from the top view, in contrast to the view of FIG. 9*c*, which is from the bottom. While grasping main body insertion instrument 100, the surgeon inserts the universal wing with wing insertion instrument 500. When the universal wing is brought into the correct position relative to the main body assembly, bolt 812 can be inserted into hole 408 of the tissue expander 407, and by rotation of the driver knob 50 of FIG. in a clockwise direction, driver 555 can rotate bolt 812 thereby engaging threads of the threaded end 815 with the threads of hole 408. Alternatively, if the threaded portions 815 of bolt 812 and hole 408 have left-handed threads, then driver knob 50 should be rotated in a counter-clockwise direction to engage bolt 812 with threaded hole 408. Before tightening bolt 812, it can be desirable to urge universal wing 800 medially or closer to main body wing 401 to provide a desired degree of support of spinous processes L1D and L2D. Once in the proper position, bolt 812 can be tightened, and the insertion instrument 100 and 500 are removed, the incisions sutured and closed.

Figure 13:
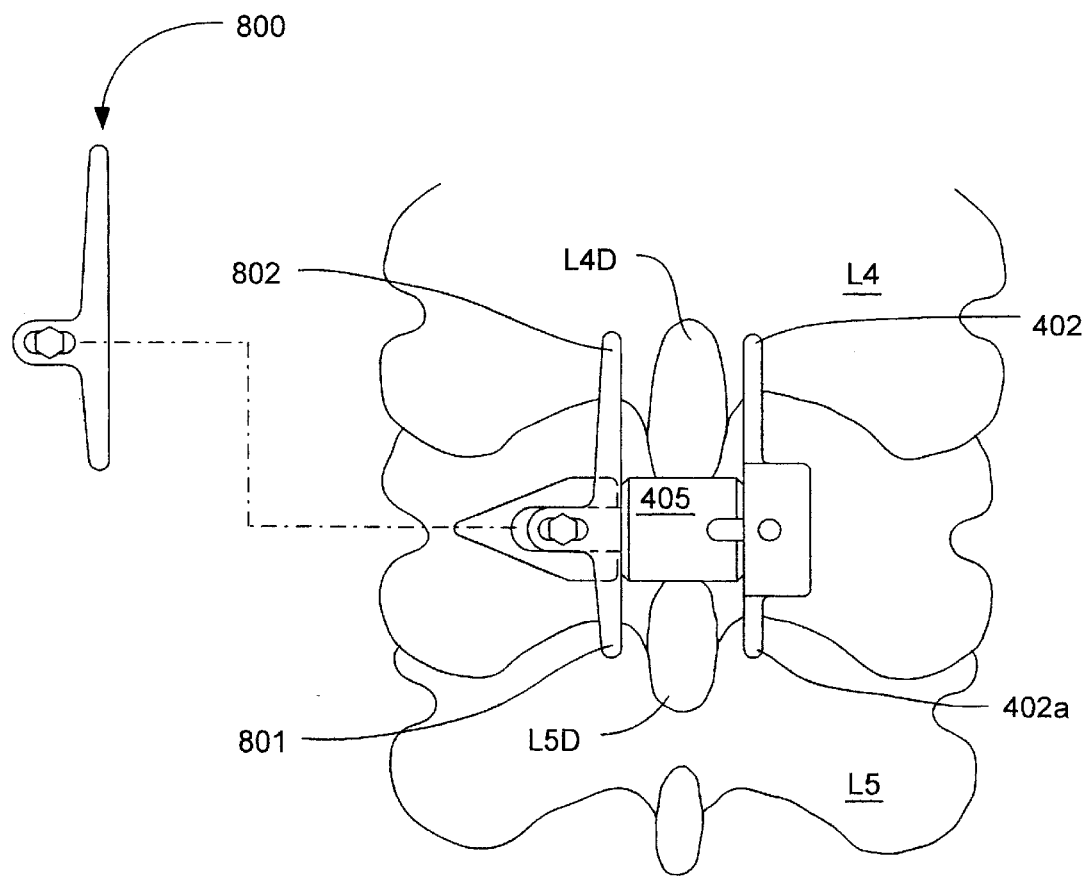
FIG. 13 depicts a dorsal view of a spine with an embodiment of a main body assembly of the invention inserted between spinous processes of adjacent vertebrae, and showing the insertion of an embodiment of a universal wing of the invention and its attachment to the embodiment of main body assembly of the invention.

FIG. 13 depicts a dorsal view of the spine of a patient, depicting an installed main body assembly 400 with universal wing 800 attached thereto. Universal wing portion 802 is shown oriented in the cephalad direction, as is main body wing portion 402. Caudad wing portions 801 and 402*a* are shown oriented in the caudal direction. Wing element 400, 402*a* are shown near the right lateral surface of the spinous process. Universal wing 800 is shown placed near the left lateral surfaces of the spinous process. Adjustment of the spacing between universal wing 800 and the spinous process is accomplished by urging the wing medially before tightening bolt 812 in oblong mounting ring 817.

V. Alternative Insertion Instrument Sets

FIGS. 14 through 17 depict alternative instrument sets of the invention. The aspects of these instrument sets, that are similar to the above described inventive instrument sets, are similarly numbered. Further, the description of the previously described instrument sets applies equally well to these alternative embodiments of the present invention.

Figure 14:
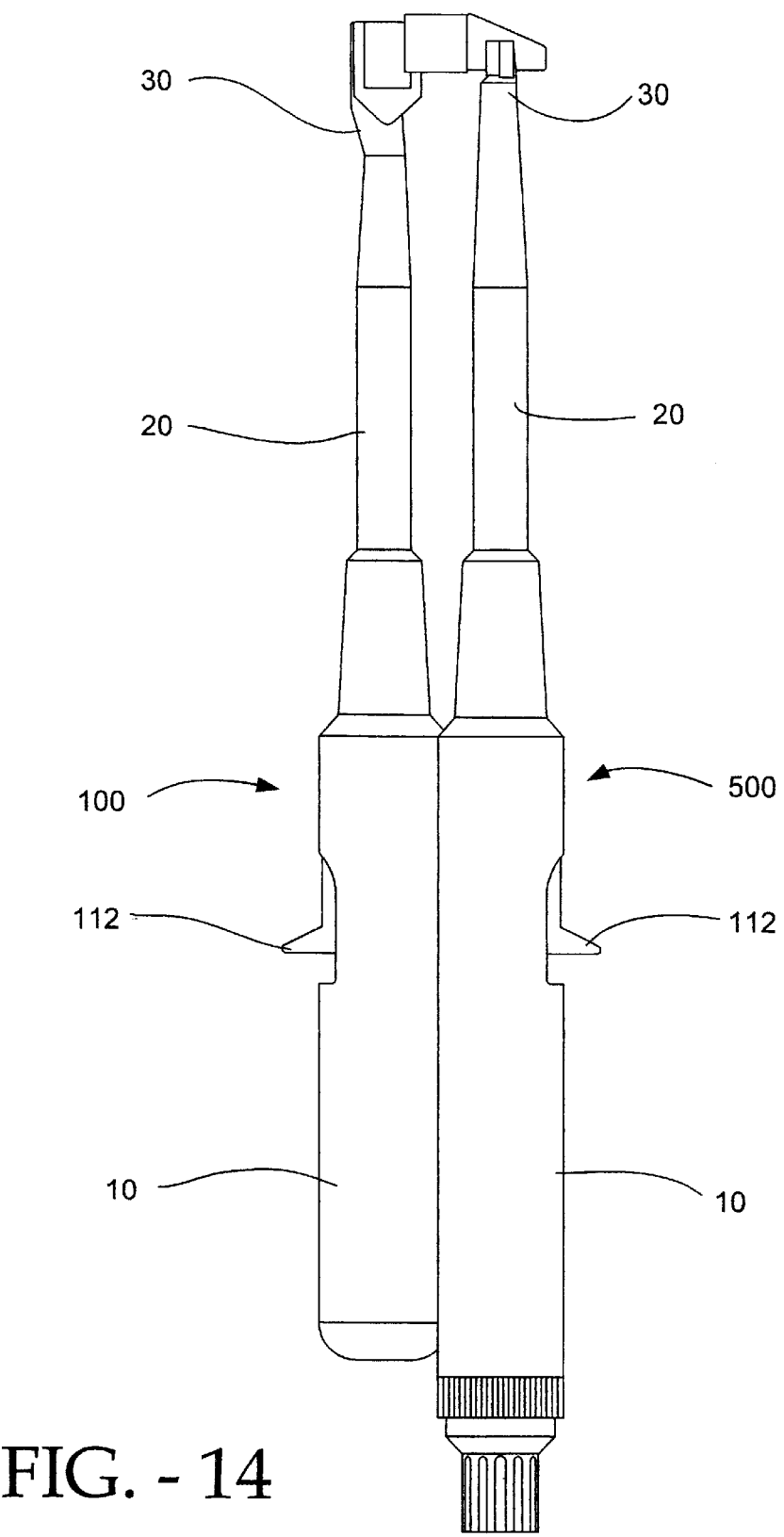
FIG. 14 depicts an alternative embodiment of instruments of the present invention with the handle of the main body insertion instrument nested into an alternate embodiment of the wing insertion instrument of the invention.
Figure 15:
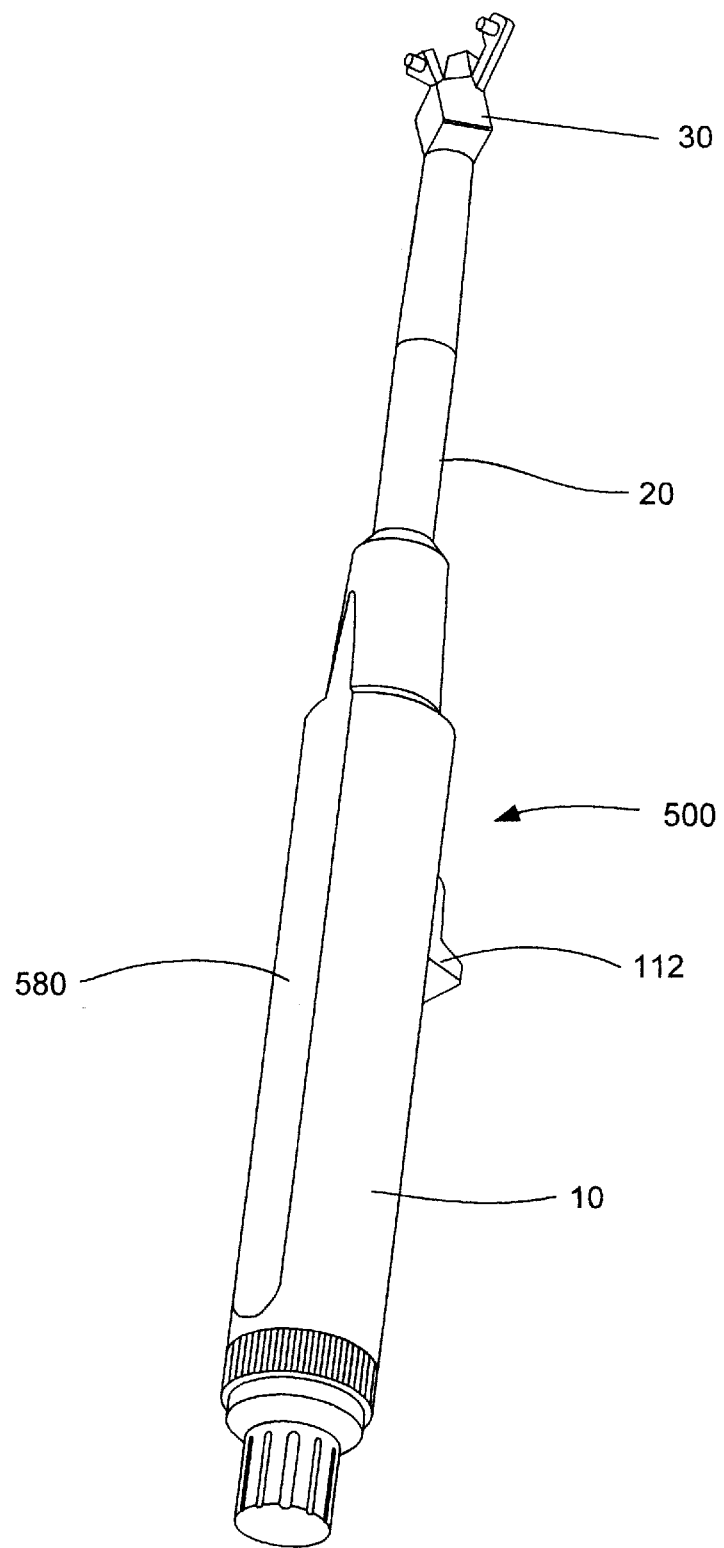
FIG. 15 depicts the wing insertion instrument of FIG. 14.

In FIG. 14 the main body insertion instrument 100 is shown nested to the wing insertion instrument 500. Both instruments together hold an implant 400. With respect to the main body insertion instrument 100 in this embodiment, this insertion instrument 100 is essentially identical to that shown in FIG. 1. The wing insertion instrument 500 has been modified to include an elongated concave recess 580 (FIG. 15) which extends, in this preferred embodiment, for substantially the length of the handle 10. This elongated concave recess 580 is shaped to conform to the outer surface of the handle 10 of the main body insertion instrument 100. Accordingly the handle 10 of the main body insertion instrument 100 can be nested in this recess 580 so that the main body insertion instrument can be mated and nested to the wing insertion instrument 500. (FIGS. 14, 15). This nesting affords the ability of the handles to align with each other so that the wing carried by the wing insertion instrument 500 can be slid into place relative to and aligned with the main body carried by the main body insertion instrument 100, as the instrument 500 is slid along the handle of instrument 100.

Figure 16:
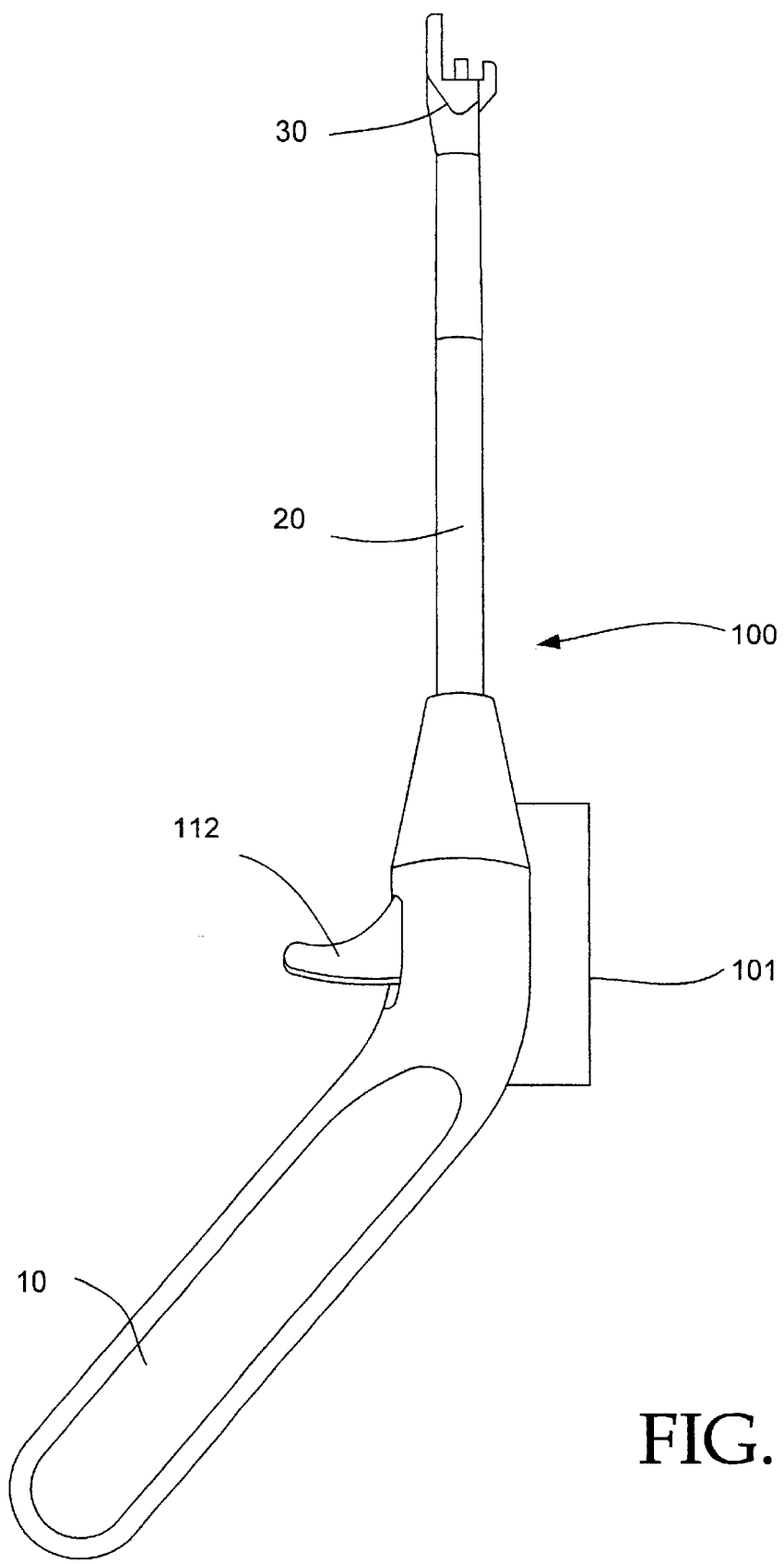
FIG. 16 depicts an alternative embodiment of the main body insertion instrument.
Figure 17:
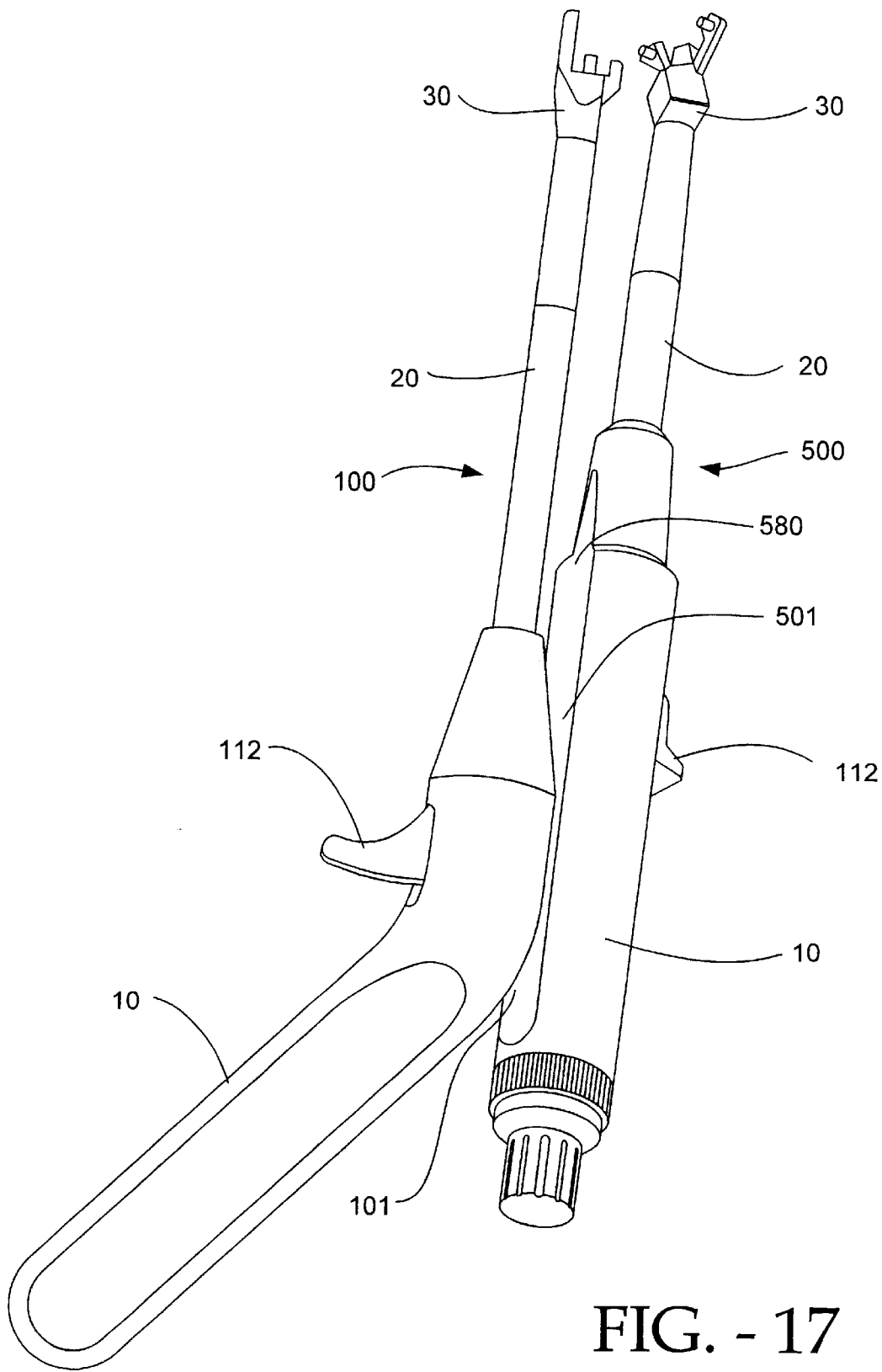
FIG. 17 depicts the alternative embodiment of the main body insertion instrument of FIG. 16 nested into the wing insertion instrument of FIG. 15.

FIGS. 16 and 17 depict yet a further alternative embodiment of the instrument set including a main body insertion instrument 100, and a wing insertion instrument 500. The main body insertion element 100 in this embodiment includes an offset handle 10 which is depicted as offset from the shaft by about 45 degrees. It has been understood that greater and lesser offsets can be accomplished and be within the spirit and scope of the invention. The offsets servers two functions. The first function is that it gives the surgeon greater leverage in manipulating and positioning the main body of the implant through the ligaments associated with the spinous processes and eventually the spinous processes themselves. This additional leverage allows the physician to urge the main body of the implant into position.

Also it can be seen in FIG. 16, the main body insertion instrument 100 includes a flange 101. This flange 101 is an additional enhancement to the insertion tool 100. It is then to be understood that the instrument set in FIGS. 16 and 17 can be fabricated without the flange 101 and the mating groove 501 of the wing insertion instrument 500 and still be within the spirit scope of the invention. As seen in FIG. 17, the mating groove 501 of the wing insertion instrument 500 is located in the recess 580.

It is to be understood that without the flange 100 and the mating groove 501, the embodiment of the insertion instrument 100 of FIG. 16 can be received in the recess 580 of the wing insertion instrument 500 of FIG. 17 as the wing insertion instrument 500 is moved relative to the main body insertion element 100 in order to align the wing relative to the main body at the surgical site.

With the flange 101 and the mating groove 501 and with the embodiment of the insertion element 100 of FIG. 16 positioned so that the main body is inserted through the spinous processes, the wing insertion instrument 500 can be mated over the main body insertion instrument 100 with the flange received in the mating groove 501. After this is accomplished, the wing insertion instrument 500 can be slid relative to the main body insertion instrument 100 in order to bring the wing into contact with and aligned with the main body. After this has occurred, the wing can be fastened to the main body.

It is to be understood that the wing insertion instrument 500 can also have an offset handle like the offset handle of main body insertion instrument 100 of FIG. 17.

It is to be understood that other devices and methods for mating and aligning insertion instrument 100 with the wing insertion instrument 500 can be envisioned and be within the spirit and scope of the invention.

INDUSTRIAL APPLICABILITY

Accordingly, it is evident that the insertion instruments, implants and methods disclosed can be said to relieve pain associated with the spine.

The above descriptions are for illustrative purposes and are not intended to be limiting to the scope of the invention. It is contemplated that instruments having locking pins and alignment pins can have other configurations. Further, the implant can have other configurations. It is also contemplated that the additional methods of using the instruments with the implants described as well as with other implants are possible, and all such embodiments are considered to be within the scope of this invention.

What is claimed is:

1. An insertion device adapted for installing a main body assembly in the spine, said device comprising:
    an elongated body having a longitudinal body axis;
    a proximal end having a handle; and
    a distal end having an insertion tip comprising:
        at least one alignment pin; and
        a locking mechanism adapted to engage a main body assembly; and
    an alignment mechanism adapted to mate with another insertion device.

2. The insertion device of claim 1 wherein said alignment mechanism includes a flange.

3. The insertion device of claim 1 wherein said alignment mechanism includes a recess.

4. The insertion device of claim 1 wherein said alignment mechanism includes a recess than extends along the elongated body.

5. The insertion device of claim 1 wherein said alignment mechanism includes a recess with a groove extending from the recess.

6. An insertion device adapted for installing a main body assembly in the spine, said device comprising:
    an elongated body having a longitudinal body axis;
    a proximal end having a handle; and
    a distal end having an insertion tip comprising:
        at least one alignment pin that is perpendicular to said longitudinal body axis; and
        a locking mechanism adapted to engage a main body assembly; and
        wherein said handle is offset at an angle to the elongated body.

7. The insertion device of claim 6 wherein said offset handle is offset at about 45 degrees from the elongated body.

8. An insertion device adapted for installing a main body assembly in the spine, said device comprising:
    an elongated body having a longitudinal body axis;
    a proximal end having a handle; and
    a distal end having an insertion tip comprising:
        at least one alignment pin; and
        a locking mechanism adapted to engage a main body assembly; and
        an alignment mechanism adapted to mate with another insertion device;
    wherein said handle is offset at an angle to the elongated body.

9. An insertion device adapted for installing a main body assembly in the spine, said device comprising:
    an elongated body having a longitudinal body axis;
    a proximal end having a handle; and
    a distal end having an insertion tip comprising:
        two alignment pins that are perpendicular to said longitudinal body axis; and
        a spring loaded locking mechanism having first and second locking pins adapted to engage said main body assembly; and
        an alignment mechanism adapted to mate with another insertion tool.

10. The insertion device of claim 9 wherein said alignment mechanism includes a flange.

11. The insertion device of claim 9 wherein said alignment mechanism includes a recess.

12. The insertion device of claim 9 wherein said alignment mechanism includes a recess than extends along the elongated body.

13. The insertion device of claim 9 wherein said alignment mechanism includes a recess with a groove extending from the recess.

14. An insertion device adapted for installing a main body assembly in the spine, said device comprising:
    an elongated body having a longitudinal body axis;
    a proximal end having a handle; and
    a distal end having an insertion tip comprising:
        two alignment pins that are perpendicular to said longitudinal body axis; and
        a spring loaded locking mechanism having first and second locking pins adapted to engage said main body assembly; and wherein said handle is offset at an angle to the elongated body.

15. The insertion device of claim 14 further including an alignment mechanism adapted to mate with another insertion device.

16. The insertion device of claim 14 wherein said offset handle is offset at about 45 degrees from the elongated body.

17. An insertion device adapted for installing a wing on a main body assembly positioned in the spine, said device comprising:
 an elongated body having a longitudinal body axis;
 a proximal end having a handle; and
 a distal end having an insertion tip comprising:
  at least one alignment pin; and
  a rotatable engagement head; and
  an alignment mechanism adapted to mate with another insertion tool.

18. The insertion device of claim 17 wherein said alignment mechanism includes a flange.

19. The insertion device of claim 17 wherein said alignment mechanism includes a recess.

20. The insertion device of claim 17 wherein said alignment mechanism includes a recess than extends along the elongated body.

21. The insertion device of claim 17 wherein said alignment mechanism includes a recess with a groove extending from the recess.

22. An insertion device adapted for installing a wing on a main body assembly positioned in the spine, said device comprising:
 an elongated body having a longitudinal body axis;
 a proximal end having a handle; and
 a distal end having an insertion tip comprising:
  at least one alignment pin that is perpendicular to said longitudinal body axis; and
  a rotatable engagement head; and
  wherein said handle is offset at an angle to the elongated body.

23. The insertion device of claim 22 wherein said offset handle is offset at about 45 degrees from the elongated body.

24. An insertion device adapted for installing a wing on a main body assembly positioned in the spine, said device comprising:
 an elongated body having a longitudinal body axis;
 a proximal end having a handle; and
 a distal end having an insertion tip comprising:
  at least one alignment pin; and
  a rotatable engagement head; and
  an alignment mechanism adapted to mate with another insertion device;
 wherein said handle is offset at an angle to the elongated body.

25. An insertion device for installing awing on a main body assembly positioned in the spine, said device comprising:
 an elongated body having a longitudinal body axis;
 a proximal end having a handle and a turning knob; and
 a distal end having an insertion tip comprising:
  two alignment pins; and
  a spring loaded, rotatable engagement head operably coupled to said turning knob and adapted to engage a rotatable component of said main body assembly; and
  an alignment mechanism adapted to mate with another insertion tool.

26. The insertion device of claim 25 wherein said alignment mechanism includes a flange.

27. The insertion device of claim 25 wherein said alignment mechanism includes a recess.

28. The insertion device of claim 25 wherein said alignment mechanism includes a recess than extends along the elongated body.

29. The insertion device of claim 25 wherein said alignment mechanism includes a recess with a groove extending from the recess.

30. An insertion device for installing a wing on a main body assembly positioned in the spine, said device comprising:
 an elongated body having a longitudinal body axis;
 a proximal end having a handle and a turning knob; and
 distal end having an insertion tip comprising:
  two alignment pins; and
  a spring loaded, rotatable engagement head operably coupled to said turning knob and adapted to engage a rotatable component of said main body assembly; and
  wherein said handle is offset at an angle to the elongated body.

31. The insertion device of claim 30 further including an alignment mechanism adapted to mate with another insertion device.

32. The insertion device of claim 30 wherein said offset handle is offset at about 45 degrees from the elongated body.

33. A system with a device for insertion of a main body assembly in the spine of a patient and a main body assembly, comprising:
 (a) a main body assembly insertion device comprising:
  (1) at least one alignment pin;
  (2) a locking mechanism; and
  (3) an alignment mechanism adapted to mate with another insertion tool;
 (b) a main body assembly comprising:
  (1) a body portion having a longitudinal axis and a first end having a wing having at least one alignment hole; and
  (2) a spacer received over said longitudinal axis, said spacer being rotatable about said axis, said spacer having a second alignment hole;
 (c) wherein said at least one alignment pin of the insertion device is selecting engageable with at least one of said alignment holes on the wing of said body portion; and
 (d) wherein said locking mechanism is selectably engageable with the second alignment hole of said spacer.

34. A system with a device for insertion of a main body assembly in the spine of a patient and a main body assembly, comprising:
 (a) a main body assembly insertion device comprising:
  (1) at least one alignment pin;
  (2) a locking mechanism; and
  (3) a handle that is offset at an angle;
 (b) a main body assembly comprising:
  (1) a body portion having a longitudinal axis and a first end having a wing having at least one alignment hole;
  (2) a spacer received over said longitudinal axis, said spacer being rotatable about said axis, said spacer having a second alignment hole; and
 (c) wherein said at least one alignment pin of the insertion device is selecting engageable with at least one of said alignment holes on the wing of said body portion; and (d) wherein said locking mechanism is selectably engageable with the second alignment hole of said spacer.

35. A system with a device for inserting a wing on a main body assembly positioned in the spine of a patient, said device and wing comprising:
(a) a wing insertion device having
(1) at least one alignment pin;
(2) a rotatable engagement head; and
(3) an alignment mechanism adapted to mate with another insertion device;
(b) a wing having:
(1) a wing plane and having at least one alignment hole; and
(2) a wing implant locking mechanism having:
(i) a first element adapted to receive said rotatable engagement head;
(ii) a second element adapted to engage with a main body assembly, said locking mechanism aligned substantially parallel to said wing plane, said locking mechanism being rotatable with respect to said wing;
(c) wherein said at least one alignment pin of said device is selectively engageable with said alignment hole of said wing; and
(d) wherein said rotatable engagement head of said device is selectably engageable with the first element of said wing implant locking mechanism.

36. A system with a device for inserting a wing on a main body assembly positioned in the spine of a patient, said device and wing comprising:
(a) a wing insertion device having
(1) at least one alignment pin;
(2) a rotatable engagement head; and
(3) a handle that is offset at an angle;
(b) a wing having:
(1) a wing plane and having at least one alignment hole; and
(2) a wing implant locking mechanism having:
(i) a first element adapted to receive said rotatable engagement head;
(ii) a second element adapted to engage with a main body assembly, said locking mechanism aligned substantially parallel to said wing plane, said locking mechanism being rotatable with respect to said wing;
(c) wherein said at least one alignment pin of said device is selectively engageable with said alignment hole of said wing; and
(d) wherein said rotatable engagement head of said device is selectably engageable with the first element of said wing implant locking mechanism.

37. An improved insertion tool for implanting an implant relative to the spine, the improvement comprising:
an alignment pin; and
a locking pin; and
an alignment mechanism adapted to mate with another insertion device.

38. An improved insertion tool for implanting an implant relative to the spine, the improvement comprising:
an alignment pin; and
an engagement head that is rotatable relative to said alignment pin; and
including a handle offset at an angle.

39. An improved insertion tool for implanting an implant having a rotatable spacer relative to the spine, the improvement comprising:
an alignment pin;
a locking pin; and
an engagement pin that is adapted to engage the rotatable spacer; and
including a handle offset at an angle.

40. An improved insertion tool for implanting an implant relative to the spine, the improvement comprising:
an alignment pin; and
a rotatable engagement head; and
an alignment mechanism adapted to mate with another insertion device.

41. A method of inserting a two piece implant into a patient comprising the steps of:
connecting a first insertion device to a first piece of the implant;
connecting a second insertion device to a second piece of the implant;
inserting the first piece into the patient with the first insertion device;
inserting the second piece into the patient with the second insertion device and before or during the second piece inserting step mating the first and second insertion device together;
using the second insertion device to connect the second piece of the implant to the first piece of the implant; and
disengaging the first insertion device from the first piece and the second insertion device from the second piece.

42. An insertion system for inserting a two piece implant into the spine comprising:
a main body insertion instrument adapted for engaging a main body;
a wing insertion instrument adapted for engaging a wing that is to be affixed to the main body;
wherein main body insertion instrument and the wing insertion instrument can mate together in order to assemble the two piece implant.

43. The system of claim 42 wherein:
one of said main body insertion instrument and the wing insertion instrument has a recess for receiving the other of said main body insertion instrument and the wing insertion instrument such that the instruments can be mated together.

44. The system of claim 42 wherein:
one of said main body insertion instrument and the wing insertion instrument has a flange that can be received in the other of said main body insertion instrument and the wing insertion instrument such that the instruments can be mated together.

45. An insertion and two piece implant system for inserting the two piece implant into the spine comprising:
a main body insertion instrument and a main body, and wherein the main body can be mounted to the main body insertion instrument;
a wing insertion instrument and a wing that is to be affixed to the main body, and wherein the wing can be mounted to the wing insertion instrument;
wherein main body insertion instrument and the wing insertion instrument can mate together in order to assemble the two piece implant.

46. The system of claim 45 wherein:
one of said main body insertion instrument and the wing insertion instrument has a recess for receiving the other of said main body insertion instrument and the wing insertion instrument such that the instruments can be mated together.

47. The system of claim 45 wherein:
one of said main body insertion instrument and the wing insertion instrument has a flange that can be received in the other of said main body insertion instrument and the wing insertion instrument such that the instruments can be mated together.

48. A method for insertion a two piece implant between adjacent spinous processes comprising the steps of:
connecting a first insertion device to a first piece of the implant and connecting a second insertion device to a second piece of the implant;
inserting the first piece of the implant into the patient with the first insertion device to a location between the adjacent spinous processes and inserting the second piece of the implant into the patient with the second insertion device to a location adjacent to the first implant and to the spinous processes, and before or during the second piece insertion step mating the first and the second insertion devices together; and
using one or both of the insertion devices to secure the first and the second pieces of the implant together; and
removing the insertion devices.

49. An insertion device adapted for installing an implant or part of an implant adjacent to spinous processes comprising:
an elongated body;
a proximal end having a handle;
a distal end adapted to engage the implant or the part of the implant for insertion of the implant or part of the implant adjacent to spinous processes; and
an alignment mechanism adapted to mate with another insertion device.

50. An insertion device adapted for installing an implant or part of an implant adjacent to spinous processes comprising:
an elongated body;
a proximal end having a handle; and
a distal end adapted to engage the implant or part of the implant for insertion of the implant or part of the implant adjacent to spinous processes;
said distal end including:
at least one alignment pin fixed to and offset from the elongated body by an angle; and
wherein said handle is offset from the elongated body by an angle in order to assist in the placement of the implant or part of the implant adjacent to the spinous processes.

51. An insertion device adapted for installing an implant having a rotatable spacer or part of an implant having a rotatable spacer adjacent to spinous processes comprising:
an elongated body;
a bore within said elongated body;
a proximal end of said elongated body having a handle;
a distal end of said elongated body being adapted to engage the implant or part of the implant for insertion of the implant or part of the implant adjacent to spinous processes, said distal end including:
a flat surface forming a plane approximately parallel to an axis of the bore; and
two alignment pins protruding from said flat surface; and
a retractable insertion rod within said bore adapted to be extended from said distal end for further engaging the implant or part of the implant, said retractable insertion rod including a first end that has a locking pin and a spacer engagement pin adapted to limit the rotation of said spacer relative to said alignment pins.

52. The insertion device of claim 51, wherein said handle is offset from the elongated body by an angle in order to assist in the placement of the implant or part of the implant adjacent to the spinous processes.

53. The insertion device of claim 51, further comprising a switch adapted to selectably extend or retract said retractable insertion rod.

54. The insertion device of claim 53, further comprising a spring attached to a second end of said insertion rod, said spring biasing said insertion rod such that said insertion rod extends from said distal end.

55. An insertion device adapted for installing an implant having a rotatable spacer adjacent to spinous processes comprising:
an elongated body having a longitudinal body axis;
a proximal end of the elongated body being adapted to be used as a handle;
a distal end of the elongated body being adapted to engage the implant for insertion of the implant adjacent to spinous processes, the distal end including:
a flat surface forming a plane approximately parallel to the longitudinal body axis; and
two alignment pins protruding from the flat surface;
a bore within the elongated body having an axis approximately parallel to the longitudinal body axis; and
a retractable insertion rod within the bore adapted to be extended from the distal end for further engaging the implant, the retractable insertion rod including a first end that has a locking pin and a spacer engagement pin adapted to limit the rotation of the spacer relative to the alignment pins.

56. The insertion device of claim 55, wherein the handle is offset from the elongated body by an angle in order to assist in the placement of the implant adjacent to the spinous processes.

57. The insertion device of claim 55, further comprising a switch for selectably extending or retracting the retractable insertion rod.

58. The insertion device of claim 57, further comprising a spring attached to a second end of the insertion rod such that the spring biases the insertion rod toward the distal end.

59. An insertion device adapted for installing an implant having a rotatable spacer adjacent to spinous processes comprising:
an elongated body having a longitudinal body axis;
a proximal end having a handle;
a distal end having an insertion tip including at least one alignment pin;
a bore within the elongated body having an axis approximately parallel to the longitudinal body axis; and
a retractable insertion rod within the bore adapted to be selectably extended from the distal end for locking the implant into place, the retractable insertion rod including a first end that has a locking pin and a spacer engagement pin adapted to limit the rotation of said spacer relative to said alignment pin.

60. The insertion device of claim 59, wherein said handle is offset from the elongated body by an angle in order to assist in the placement of the implant adjacent to the spinous processes.

61. The insertion device of claim 59, further comprising a switch for selectably extending or retracting said retractable insertion rod.

62. The insertion device of claim 61, further comprising a spring attached to a second end of said insertion rod such that said spring biases the insertion rod toward the distal end.

* * * * *